(12) United States Patent
Mertens et al.

(10) Patent No.: US 8,586,538 B2
(45) Date of Patent: Nov. 19, 2013

(54) METHOD OF TREATING A PATIENT SUFFERING FROM A BLEEDING DISORDER COMPRISING ADMINISTERING AN ANTIBODY AGAINST THE A3-C1 OF FVIII

(75) Inventors: Koenraad Mertens, Leiden (NL); Arend N. Bovenschen, Utrecht (NL); Jan Voorberg, Wormer (NL); Manfred Rieger, Gaenserndorf (AT); Friedrich Scheiflinger, Vienna (AT)

(73) Assignee: Stichting Sanquin Bloedvoorziening, Amsterdam (NL)

( * ) Notice: Subject to any disclaimer, the term of this patent is extended or adjusted under 35 U.S.C. 154(b) by 2143 days.

(21) Appl. No.: 10/512,907

(22) PCT Filed: Apr. 28, 2003

(86) PCT No.: PCT/EP03/04425
§ 371 (c)(1),
(2), (4) Date: Nov. 4, 2005

(87) PCT Pub. No.: WO03/093313
PCT Pub. Date: Nov. 13, 2003

(65) Prior Publication Data
US 2008/0219983 A1    Sep. 11, 2008

Related U.S. Application Data

(60) Provisional application No. 60/376,351, filed on Apr. 29, 2002.

(51) Int. Cl.
*A61K 38/36* (2006.01)
*A61K 38/37* (2006.01)
*A61K 39/00* (2006.01)

(52) U.S. Cl.
USPC .... 514/13.7; 514/14.1; 424/184.1; 424/185.1

(58) Field of Classification Search
None
See application file for complete search history.

(56) References Cited

FOREIGN PATENT DOCUMENTS

WO    WO 96/41816    12/1996

OTHER PUBLICATIONS

Neels et al., Trends Cardiovasc Med. 10: 8-14, 2000.*
Girolami et al , J. Thromb Thrombylysis 21: 175-178, 2006.*
Kailas et al., Hemophilia, 7: 375-380, 2001.*
van den Brink et al., Blood 97: 966-972, 2001.*
Meems et al., Blood 114(18): 3938-3946 (2009).
Bovenschen et al., Blood 101(10): 3933-3939 (2003).
Lenting et al., The Journal of Biological Chemistry 271(4): 1935-1940 (1996).
Saenko et al., The Journal of Biological Chemistry 274(53): 37685-37692 (1999).

* cited by examiner

*Primary Examiner* — Gyan Chandra
(74) *Attorney, Agent, or Firm* — Perkins Coie LLP

(57) ABSTRACT

The present invention concerns the use of peptides derived from and antibodies generated against Factor VIII and the inhibition of Factor VIII interaction with LRP. Furthermore, the present invention concerns a method to inhibit LRP interaction with Factor VIII as well as a method to decrease Factor VIII degradation and/or prolong Factor VIII half-life in a biological fluid and/or a method to treat patients suffering from a blood coagulation disorder, especially Haemophilia A. The present invention also concerns a pharmaceutical composition useful for the decrease of Factor VIII degradation in a biological fluid, the inhibition of Factor VIII interaction with LRP, and/or the prolongation of Factor VIII half-life in a biological fluid for treatment of a blood coagulation disorder, especially Haemophilia A.

5 Claims, 8 Drawing Sheets

Figure 1:
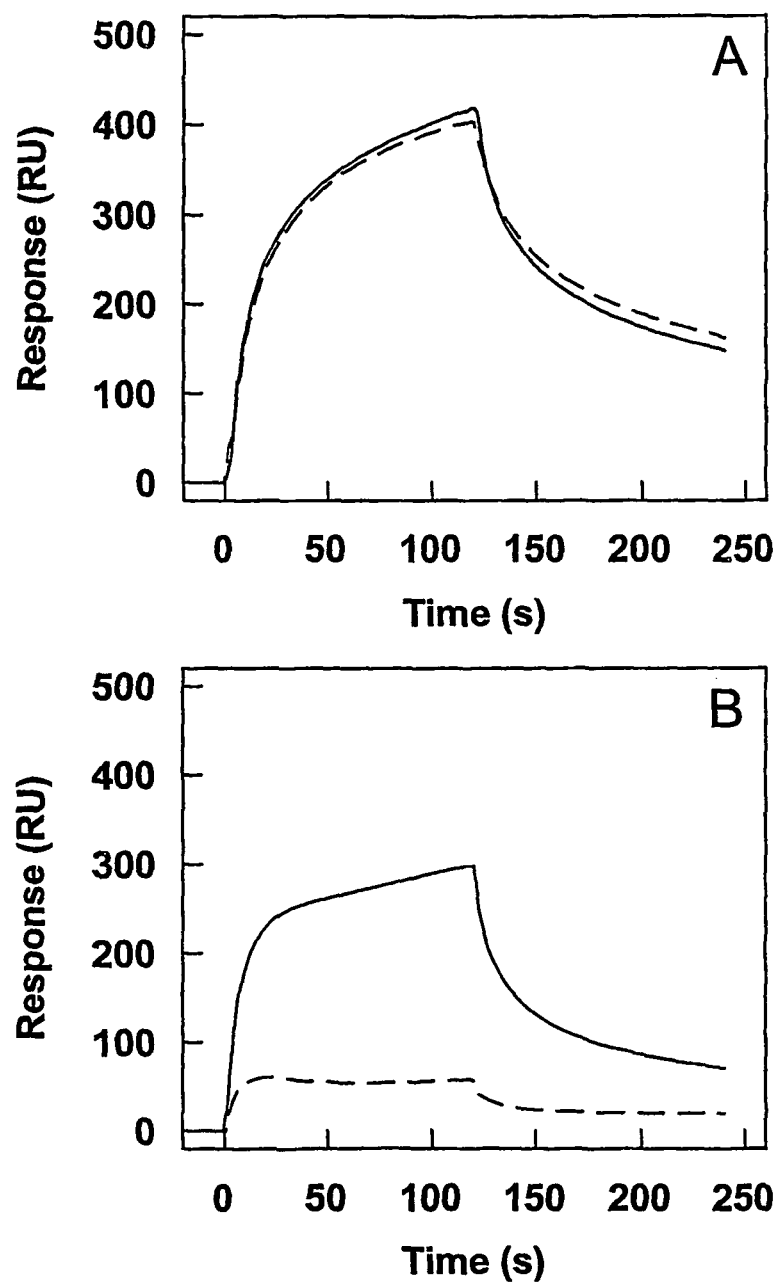

SEQUENCE LISTING

<160> NUMBER OF SEQ ID NOS: 26

<210> SEQ ID NO 1
<211> LENGTH: 8
<212> TYPE: PRT
<213> ORGANISM: Artificial Sequence
<220> FEATURE:
<223> OTHER INFORMATION: Description of Artificial
      Sequence:1811-Glu-1818-Lys peptide derived from
      human Factor VIII A3 domain region

<400> SEQUENCE: 1

Glu Thr Lys Thr Tyr Phe Trp Lys
 1               5

<210> SEQ ID NO 2
<211> LENGTH: 15
<212> TYPE: PRT
<213> ORGANISM: Artificial Sequence
<220> FEATURE:
<223> OTHER INFORMATION: Description of Artificial
      Sequence:1804-Lys-1818-Lys peptide derived from
      human Factor VIII A3 domain region

<400> SEQUENCE: 2

Lys Asn Phe Val Lys Pro Asn Glu Thr Lys Thr Tyr Phe Trp Lys
 1               5                  10                  15

<210> SEQ ID NO 3
<211> LENGTH: 20
<212> TYPE: PRT
<213> ORGANISM: Artificial Sequence
<220> FEATURE:
<223> OTHER INFORMATION: Description of Artificial
      Sequence:1815-Tyr-1834-Ala peptide derived from
      human Factor VIII A3 domain region

<400> SEQUENCE: 3

Tyr Phe Trp Lys Val Gln His His Met Ala Pro Thr Lys Asp Glu Phe
 1               5                  10                  15

Asp Cys Lys Ala
            20

<210> SEQ ID NO 4
<211> LENGTH: 31
<212> TYPE: PRT
<213> ORGANISM: Artificial Sequence
<220> FEATURE:
<223> OTHER INFORMATION: Description of Artificial
      Sequence:1804-Lys-1834-Ala peptide derived from
      human Factor VIII A3 domain region

<400> SEQUENCE: 4

Lys Asn Phe Val Lys Pro Asn Glu Thr Lys Thr Tyr Phe Trp Lys Val
 1               5                  10                  15

Gln His His Met Ala Pro Thr Lys Asp Glu Phe Asp Cys Lys Ala
            20                  25                  30

<210> SEQ ID NO 5
<211> LENGTH: 15
<212> TYPE: PRT
<213> ORGANISM: Artificial Sequence
<220> FEATURE:
<223> OTHER INFORMATION: Description of Artificial
      Sequence:1707-Trp-1721-Arg peptide derived from
      human Factor VIII A3 domain region

```
<400> SEQUENCE: 5

Trp Asp Tyr Gly Met Ser Ser Ser Pro His Val Leu Arg Asn Arg
1               5                   10                  15

<210> SEQ ID NO 6
<211> LENGTH: 13
<212> TYPE: PRT
<213> ORGANISM: Artificial Sequence
<220> FEATURE:
<223> OTHER INFORMATION: Description of Artificial
      Sequence:1822-His-1834-Ala peptide derived from
      human Factor VIII A3 domain region

<400> SEQUENCE: 6

His Met Ala Pro Thr Lys Asp Glu Phe Asp Cys Lys Ala
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial
      Sequence:1892-Thr-1901-Ala peptide derived from
      human Factor VIII A3 domain region

<400> SEQUENCE: 7

Thr Glu Asn Met Glu Arg Asn Cys Arg Ala
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial
      Sequence:1908-Glu-1919-His peptide derived from
      human Factor VIII A3 domain region

<400> SEQUENCE: 8

Glu Asp Pro Thr Phe Lys Glu Asn Tyr Arg Phe His
1               5                   10

<210> SEQ ID NO 9
<211> LENGTH: 9
<212> TYPE: PRT
<213> ORGANISM: Artificial Sequence
<220> FEATURE:
<223> OTHER INFORMATION: Description of Artificial
      Sequence:1964-Thr-1972-Lys peptide derived from
      human Factor VIII A3 domain region

<400> SEQUENCE: 9

Thr Val Arg Lys Lys Glu Glu Tyr Lys
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial
      Sequence:2049-Lys-2057-Gly peptide derived from
      human Factor VIII C1 domain region

<400> SEQUENCE: 10

Lys Leu Ala Arg Leu His Tyr Ser Gly
1               5
```

```
<210> SEQ ID NO 11
<211> LENGTH: 10
<212> TYPE: PRT
<213> ORGANISM: Artificial Sequence
<220> FEATURE:
<223> OTHER INFORMATION: Description of Artificial
      Sequence:2108-Asp-2117-Gly peptide derived from
      human Factor VIII C1 domain region

<400> SEQUENCE: 11

Asp Gly Lys Lys Trp Gln Thr Tyr Arg Gly
1               5                   10

<210> SEQ ID NO 12
<211> LENGTH: 8
<212> TYPE: PRT
<213> ORGANISM: Artificial Sequence
<220> FEATURE:
<223> OTHER INFORMATION: Description of Artificial
      Sequence:1704-Ser-1711-His peptide derived from
      human Factor V

<400> SEQUENCE: 12

Ser Ser Tyr Thr Tyr Val Trp His
1               5

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence:polymerase
      chain reaction sense oligonucleotide primer for
      1649-Glu-2172-Asn of human Factor VIII

<400> SEQUENCE: 13
ttactcgagg aaataactcg tactactc                                        28

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence:polymerase
      chain reaction anti-sense oligonucleotide primer
      for 1649-Glu-2172-Asn of human Factor VIII

<400> SEQUENCE: 14
aatgcggccg cttcaattta aatcacagcc cat                                  33

<210> SEQ ID NO 15
<211> LENGTH: 72
<212> TYPE: DNA
<213> ORGANISM: Artificial Sequence
<220> FEATURE:
<223> OTHER INFORMATION: Description of Artificial Sequence:DNA fragment
      encoding poly His tag

<400> SEQUENCE: 15
attggatccg gccatcatca tcatcatcat ggcggcagcc cccgcagctt tcaaaagccc    60
ggggccatgg ga                                                         72

<210> SEQ ID NO 16
<211> LENGTH: 378
<212> TYPE: DNA
<213> ORGANISM: Homo sapiens
<220> FEATURE:
<223> OTHER INFORMATION: heavy chain of scFV KM41
```

```
<220> FEATURE:
<221> NAME/KEY: CDS
<222> LOCATION: (1)..(378)
<223> OTHER INFORMATION: heavy chain of scFV KM41

<400> SEQUENCE: 16 cag gtg cag ctg ttg cag tct gcg gct gac gtg aag aag cct ggg gcc      48
Gln Val Gln Leu Leu Gln Ser Ala Ala Asp Val Lys Lys Pro Gly Ala
 1               5                  10                  15 tca gtg aag gtc tcc tgt acg gct tct gga tac atc ttc acc agt tat      96
Ser Val Lys Val Ser Cys Thr Ala Ser Gly Tyr Ile Phe Thr Ser Tyr
            20                  25                  30 gat atc gac tgg gtg cga cag gcc act gga caa ggg ctt gag tgg atg     144
Asp Ile Asp Trp Val Arg Gln Ala Thr Gly Gln Gly Leu Glu Trp Met
        35                  40                  45 gga tgg atg aat cct aac agt ggt aac gca ggc ttt gca cag aag ttt     192
Gly Trp Met Asn Pro Asn Ser Gly Asn Ala Gly Phe Ala Gln Lys Phe
    50                  55                  60 aag ggc aga ctc acc ttg acc agg gac act tcc aca agc aca gcc tac     240
Lys Gly Arg Leu Thr Leu Thr Arg Asp Thr Ser Thr Ser Thr Ala Tyr
65                  70                  75                  80 atg gag ctg agg aga ctg gaa tct gag gac acg gcc gtg tat tac tgt     288
Met Glu Leu Arg Arg Leu Glu Ser Glu Asp Thr Ala Val Tyr Tyr Cys
                85                  90                  95 gcg aga tcg acg cca cac tct tac tct ggt tcg ggc ctg ccc cct acc     336
Ala Arg Ser Thr Pro His Ser Tyr Ser Gly Ser Gly Leu Pro Pro Thr
            100                 105                 110 tct gac tcc tgg ggc cag gga acc ctg gtc acc gtg tcg agt             378
Ser Asp Ser Trp Gly Gln Gly Thr Leu Val Thr Val Ser Ser
        115                 120                 125

<210> SEQ ID NO 17
<211> LENGTH: 126
<212> TYPE: PRT
<213> ORGANISM: Homo sapiens
<220> FEATURE:
<223> OTHER INFORMATION: heavy chain of scFV KM41

<400> SEQUENCE: 17

Gln Val Gln Leu Leu Gln Ser Ala Ala Asp Val Lys Lys Pro Gly Ala
 1               5                  10                  15

Ser Val Lys Val Ser Cys Thr Ala Ser Gly Tyr Ile Phe Thr Ser Tyr
            20                  25                  30

Asp Ile Asp Trp Val Arg Gln Ala Thr Gly Gln Gly Leu Glu Trp Met
        35                  40                  45

Gly Trp Met Asn Pro Asn Ser Gly Asn Ala Gly Phe Ala Gln Lys Phe
    50                  55                  60

Lys Gly Arg Leu Thr Leu Thr Arg Asp Thr Ser Thr Ser Thr Ala Tyr
65                  70                  75                  80

Met Glu Leu Arg Arg Leu Glu Ser Glu Asp Thr Ala Val Tyr Tyr Cys
                85                  90                  95

Ala Arg Ser Thr Pro His Ser Tyr Ser Gly Ser Gly Leu Pro Pro Thr
            100                 105                 110

Ser Asp Ser Trp Gly Gln Gly Thr Leu Val Thr Val Ser Ser
        115                 120                 125

<210> SEQ ID NO 18
<211> LENGTH: 324
<212> TYPE: DNA
<213> ORGANISM: Homo sapiens
<220> FEATURE:
<223> OTHER INFORMATION: light chain of scFV KM41
```

```
<220> FEATURE:
<221> NAME/KEY: CDS
<222> LOCATION: (1)..(324)
<223> OTHER INFORMATION: light chain of scFV KM41

<400> SEQUENCE: 18 gaa att gtg ctg act cag tct cca ggc acc ctg tct ttg tct cca ggg      48
Glu Ile Val Leu Thr Gln Ser Pro Gly Thr Leu Ser Leu Ser Pro Gly
  1               5                  10                  15 gaa aga gcc acc ctc tcc tgc agg gcc agt cag agt gtt agc agc agc      96
Glu Arg Ala Thr Leu Ser Cys Arg Ala Ser Gln Ser Val Ser Ser Ser
             20                  25                  30 ttc tta ggc tgg tac caa cag aaa cct ggc cag gct ccc agg ctc ctc     144
Phe Leu Gly Trp Tyr Gln Gln Lys Pro Gly Gln Ala Pro Arg Leu Leu
         35                  40                  45 atc tat ggt gca tcc agc agg gcc act ggc atc cca gac agg ttc agt     192
Ile Tyr Gly Ala Ser Ser Arg Ala Thr Gly Ile Pro Asp Arg Phe Ser
     50                  55                  60 ggc agt ggg tct ggg aca gac ttc act ctc acc atc agc aga ctg gag     240
Gly Ser Gly Ser Gly Thr Asp Phe Thr Leu Thr Ile Ser Arg Leu Glu
 65                  70                  75                  80 cct gaa gat ttt gca gtg tat tac tgt cag cag tat ggt atc tca ccg     288
Pro Glu Asp Phe Ala Val Tyr Tyr Cys Gln Gln Tyr Gly Ile Ser Pro
                 85                  90                  95 ctc act ttc ggc gga ggg acc aag ctg gag atc aaa                     324
Leu Thr Phe Gly Gly Gly Thr Lys Leu Glu Ile Lys
            100                 105

<210> SEQ ID NO 19
<211> LENGTH: 108
<212> TYPE: PRT
<213> ORGANISM: Homo sapiens
<220> FEATURE:
<223> OTHER INFORMATION: light chain of scFV KM41

<400> SEQUENCE: 19

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
             20                  25                  30

Phe Leu Gly Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ile Ser Pro
                 85                  90                  95

Leu Thr Phe Gly Gly Gly Thr Lys Leu Glu Ile Lys
            100                 105

<210> SEQ ID NO 20
<211> LENGTH: 360
<212> TYPE: DNA
<213> ORGANISM: Homo sapiens
<220> FEATURE:
<223> OTHER INFORMATION: heavy chain of scFV KM33
<220> FEATURE:
<221> NAME/KEY: CDS
<222> LOCATION: (1)..(360)
<223> OTHER INFORMATION: heavy chain of scFV KM33

<400> SEQUENCE: 20
```

```
gag gtg cag ctg gtg gag tct ggg gga ggc gtg gtc cag cct ggg agg      48
Glu Val Gln Leu Val Glu Ser Gly Gly Gly Val Val Gln Pro Gly Arg
 1               5                  10                  15 tcc ctg aga ctc tcc tgt gta gac tct gga ctc acc ttc agt agt tat      96
Ser Leu Arg Leu Ser Cys Val Asp Ser Gly Leu Thr Phe Ser Ser Tyr
             20                  25                  30 ggc atg cac tgg gtc cgc cag gct cca ggc gcg ggg ctg gag tgg gtg     144
Gly Met His Trp Val Arg Gln Ala Pro Gly Ala Gly Leu Glu Trp Val
         35                  40                  45 gcc gtt att tca tac gac gga aat gat aaa tat tat gca gac tcc gtg     192
Ala Val Ile Ser Tyr Asp Gly Asn Asp Lys Tyr Tyr Ala Asp Ser Val
     50                  55                  60 aag ggc cga ttc gcc atc tcc aga gac aat gcc aag aac acg ctg tat     240
Lys Gly Arg Phe Ala Ile Ser Arg Asp Asn Ala Lys Asn Thr Leu Tyr
 65                  70                  75                  80 ctg caa atg aac agc ctg aca ata gag gac acg gct gtc tat tat tgt     288
Leu Gln Met Asn Ser Leu Thr Ile Glu Asp Thr Ala Val Tyr Tyr Cys
                 85                  90                  95 gcg aaa gat ctc ata gaa tca aat att gcg gag gcc ttc tgg ggc cag     336
Ala Lys Asp Leu Ile Glu Ser Asn Ile Ala Glu Ala Phe Trp Gly Gln
            100                 105                 110 gga acc ctg gtc acc gtg tcg agt                                     360
Gly Thr Leu Val Thr Val Ser Ser
            115                 120
```

<210> SEQ ID NO 21
<211> LENGTH: 120
<212> TYPE: PRT
<213> ORGANISM: Homo sapiens
<220> FEATURE:
<223> OTHER INFORMATION: heavy chain of scFV KM33

<400> SEQUENCE: 21

```
Glu Val Gln Leu Val Glu Ser Gly Gly Gly Val Val Gln Pro Gly Arg
 1               5                  10                  15

Ser Leu Arg Leu Ser Cys Val Asp Ser Gly Leu Thr Phe Ser Ser Tyr
             20                  25                  30

Gly Met His Trp Val Arg Gln Ala Pro Gly Ala Gly Leu Glu Trp Val
         35                  40                  45

Ala Val Ile Ser Tyr Asp Gly Asn Asp Lys Tyr Tyr Ala Asp Ser Val
     50                  55                  60

Lys Gly Arg Phe Ala Ile Ser Arg Asp Asn Ala Lys Asn Thr Leu Tyr
 65                  70                  75                  80

Leu Gln Met Asn Ser Leu Thr Ile Glu Asp Thr Ala Val Tyr Tyr Cys
                 85                  90                  95

Ala Lys Asp Leu Ile Glu Ser Asn Ile Ala Glu Ala Phe Trp Gly Gln
            100                 105                 110

Gly Thr Leu Val Thr Val Ser Ser
            115                 120
```

<210> SEQ ID NO 22
<211> LENGTH: 321
<212> TYPE: DNA
<213> ORGANISM: Homo sapiens
<220> FEATURE:
<223> OTHER INFORMATION: light chain of scFV KM33
<220> FEATURE:
<221> NAME/KEY: CDS
<222> LOCATION: (1)..(321)
<223> OTHER INFORMATION: heavy chain of scFV KM33

<400> SEQUENCE: 22

```
gac atc cag atg acc cag tct cca tcc tcc ctg tct gca tct gtc gga        48
Asp Ile Gln Met Thr Gln Ser Pro Ser Ser Leu Ser Ala Ser Val Gly
 1               5                  10                  15 gac aca gtc acc atc gct tgc cgg gcg agt cgc gac att aga aat gat        96
Asp Thr Val Thr Ile Ala Cys Arg Ala Ser Arg Asp Ile Arg Asn Asp
                 20                  25                  30 tta gcc tgg tat cag cag aaa cca ggg aaa gcc cct aaa ctc cta atc       144
Leu Ala Trp Tyr Gln Gln Lys Pro Gly Lys Ala Pro Lys Leu Leu Ile
             35                  40                  45 tat gct aca tcc cgt tta caa agt ggg gtc cct tca agg ttc agc ggc       192
Tyr Ala Thr Ser Arg Leu Gln Ser Gly Val Pro Ser Arg Phe Ser Gly
         50                  55                  60 agt gga tct ttc aca gat ttc act ctc acc atc aac agc cta cag cct       240
Ser Gly Ser Phe Thr Asp Phe Thr Leu Thr Ile Asn Ser Leu Gln Pro
 65                  70                  75                  80 gac gat tct gca act tat tac tgt ctc caa gat tcc gat tat ccc ctc       288
Asp Asp Ser Ala Thr Tyr Tyr Cys Leu Gln Asp Ser Asp Tyr Pro Leu
                 85                  90                  95 act ttc ggc gga ggg acc aaa gtg gat atc aaa                           321
Thr Phe Gly Gly Gly Thr Lys Val Asp Ile Lys
            100                 105
```

<210> SEQ ID NO 23
<211> LENGTH: 107
<212> TYPE: PRT
<213> ORGANISM: Homo sapiens
<220> FEATURE:
<223> OTHER INFORMATION: light chain of scFV KM33

<400> SEQUENCE: 23

```
Asp Ile Gln Met Thr Gln Ser Pro Ser Ser Leu Ser Ala Ser Val Gly
 1               5                  10                  15

Asp Thr Val Thr Ile Ala Cys Arg Ala Ser Arg Asp Ile Arg Asn Asp
                 20                  25                  30

Leu Ala Trp Tyr Gln Gln Lys Pro Gly Lys Ala Pro Lys Leu Leu Ile
             35                  40                  45

Tyr Ala Thr Ser Arg Leu Gln Ser Gly Val Pro Ser Arg Phe Ser Gly
         50                  55                  60

Ser Gly Ser Phe Thr Asp Phe Thr Leu Thr Ile Asn Ser Leu Gln Pro
 65                  70                  75                  80

Asp Asp Ser Ala Thr Tyr Tyr Cys Leu Gln Asp Ser Asp Tyr Pro Leu
                 85                  90                  95

Thr Phe Gly Gly Gly Thr Lys Val Asp Ile Lys
            100                 105
```

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence:peptide
      linker connecting light and heavy chains of KM33 scFv and
      KM41 scFv

<400> SEQUENCE: 24

```
Gly Gly Gly Gly Ser Gly Gly Gly Ser Gly Gly Gly Gly Ser
 1               5                  10                  15
```

<210> SEQ ID NO 25
<211> LENGTH: 273
<212> TYPE: PRT
<213> ORGANISM: Artificial Sequence
<220> FEATURE:

-continued

<223> OTHER INFORMATION: Description of Artificial Sequence:light and
      heavy chains of expressed scFv KM41 protein with peptide
      linker and histidine tag at C-terminus

<400> SEQUENCE: 25

Gln Val Gln Leu Leu Gln Ser Ala Ala Asp Val Lys Lys Pro Gly Ala
1               5                   10                  15

Ser Val Lys Val Ser Cys Thr Ala Ser Gly Tyr Ile Phe Thr Ser Tyr
            20                  25                  30

Asp Ile Asp Trp Val Arg Gln Ala Thr Gly Gln Gly Leu Glu Trp Met
        35                  40                  45

Gly Trp Met Asn Pro Asn Ser Gly Asn Ala Gly Phe Ala Gln Lys Phe
    50                  55                  60

Lys Gly Arg Leu Thr Leu Thr Arg Asp Thr Ser Thr Ser Thr Ala Tyr
65                  70                  75                  80

Met Glu Leu Arg Arg Leu Glu Ser Glu Asp Thr Ala Val Tyr Tyr Cys
                85                  90                  95

Ala Arg Ser Thr Pro His Ser Tyr Ser Gly Ser Gly Leu Pro Pro Thr
            100                 105                 110

Ser Asp Ser Trp Gly Gln Gly Thr Leu Val Thr Val Ser Ser Gly Gly
        115                 120                 125

Gly Gly Ser Gly Gly Gly Gly Ser Gly Gly Gly Gly Ser Glu Ile Val
    130                 135                 140

Leu Thr Gln Ser Pro Gly Thr Leu Ser Leu Ser Pro Gly Glu Arg Ala
145                 150                 155                 160

Thr Leu Ser Cys Arg Ala Ser Gln Ser Val Ser Ser Ser Phe Leu Gly
                165                 170                 175

Trp Tyr Gln Gln Lys Pro Gly Gln Ala Pro Arg Leu Leu Ile Tyr Gly
            180                 185                 190

Ala Ser Ser Arg Ala Thr Gly Ile Pro Asp Arg Phe Ser Gly Ser Gly
        195                 200                 205

Ser Gly Thr Asp Phe Thr Leu Thr Ile Ser Arg Leu Glu Pro Glu Asp
    210                 215                 220

Phe Ala Val Tyr Tyr Cys Gln Gln Tyr Gly Ile Ser Pro Leu Thr Phe
225                 230                 235                 240

Gly Gly Gly Thr Lys Leu Glu Ile Lys Arg Ala Ala Ala Glu Gln Lys
                245                 250                 255

Leu Ile Ser Glu Glu Asp Leu Asn Gly Ala Ala His His His His His
            260                 265                 270

His

<210> SEQ ID NO 26
<211> LENGTH: 266
<212> TYPE: PRT
<213> ORGANISM: Artificial Sequence
<220> FEATURE:
<223> OTHER INFORMATION: Description of Artificial Sequence:light and
      heavy chains of expressed scFv KM33 protein with peptide
      linker and histidine tag at C-terminus

<400> SEQUENCE: 26

Glu Val Gln Leu Val Glu Ser Gly Gly Gly Val Val Gln Pro Gly Arg
1               5                   10                  15

Ser Leu Arg Leu Ser Cys Val Asp Ser Gly Leu Thr Phe Ser Ser Tyr
            20                  25                  30

Gly Met His Trp Val Arg Gln Ala Pro Gly Ala Gly Leu Glu Trp Val
        35                  40                  45

```
Ala Val Ile Ser Tyr Asp Gly Asn Asp Lys Tyr Tyr Ala Asp Ser Val
     50                  55                  60
Lys Gly Arg Phe Ala Ile Ser Arg Asp Asn Ala Lys Asn Thr Leu Tyr
 65              70                  75                      80
Leu Gln Met Asn Ser Leu Thr Ile Glu Asp Thr Ala Val Tyr Tyr Cys
             85                      90                  95
Ala Lys Asp Leu Ile Glu Ser Asn Ile Ala Glu Ala Phe Trp Gly Gln
            100                 105                 110
Gly Thr Leu Val Thr Val Ser Ser Gly Gly Gly Ser Gly Gly Gly
        115             120                 125
Gly Ser Gly Gly Gly Gly Ser Asp Ile Gln Met Thr Gln Ser Pro Ser
    130                 135                 140
Ser Leu Ser Ala Ser Val Gly Asp Thr Val Thr Ile Ala Cys Arg Ala
145                 150                 155                 160
Ser Arg Asp Ile Arg Asn Asp Leu Ala Trp Tyr Gln Gln Lys Pro Gly
                165                 170                 175
Lys Ala Pro Lys Leu Leu Ile Tyr Ala Thr Ser Arg Leu Gln Ser Gly
            180                 185                 190
Val Pro Ser Arg Phe Ser Gly Ser Gly Ser Phe Thr Asp Phe Thr Leu
            195                 200                 205
Thr Ile Asn Ser Leu Gln Pro Asp Asp Ser Ala Thr Tyr Tyr Cys Leu
        210                 215                 220
Gln Asp Ser Asp Tyr Pro Leu Thr Phe Gly Gly Gly Thr Lys Val Asp
225                 230                 235                 240
Ile Lys Arg Ala Ala Ala Glu Gln Lys Leu Ile Ser Glu Glu Asp Leu
            245                 250                 255
Asn Gly Ala Ala His His His His His His
            260                 265
```

METHOD OF TREATING A PATIENT SUFFERING FROM A BLEEDING DISORDER COMPRISING ADMINISTERING AN ANTIBODY AGAINST THE A3-C1 OF FVIII

The present invention concerns the use of peptides derived from and antibodies generated against Factor VIII and the inhibition of Factor VIII interaction with LRP. Furthermore, the present invention concerns a method to inhibit LRP interaction with Factor VIII as well as a method to decrease Factor VIII degradation and/or prolong Factor VIII half-life in a biological fluid and/or a method to treat patients suffering from a blood coagulation disorder, especially Haemophilia A. The present invention also concerns a pharmaceutical composition useful for the decrease of Factor VIII degradation in a biological fluid, the inhibition of Factor VIII interaction with LRP, and/or the prolongation of Factor VIII half-life in a biological fluid for treatment of a blood coagulation disorder, especially Haemophilia A.

Blood coagulation involves a combination of different haemostatic reaction routes which finally lead to the formation of a thrombus. Thrombi are clots of blood components on the surface of the walls of vessels and mainly consist of aggregated blood platelets and insoluble cross-linked fibrin. The formation of fibrin is induced by the limited proteolysis of fibrinogen by the clotting enzyme thrombin. This enzyme is the end-product of a coagulation cascade, which is a sequence of zymogen activations that take place at the surface of activated platelets and leucocytes and a multitude of vascular cells (see e.g. K. G. Mann et al, Blood, 1990, Vol. 76, pages 1-16; incorporated herein by reference).

A key step in this coagulation cascade is the activation of Factor X by a complex of activated Factor IX (Factor IXa) and activated Factor VIII (Factor VIIIa).

Coagulation Factor VIII is thus a key protein in the intrinsic pathway of the coagulation cascade. The function of FVIII is to serve as a cofactor for the enzyme FIXa and to increase the catalytic efficiency of this protease by five to six orders of magnitude (van Dieijen al. 1981. The Journal of Biological Chemistry 256: 3433-3442; incorporated herein by reference). The importance of FVIII is demonstrated by the severe bleeding disorder Haemophilia A, which is characterised by the absence of active FVIII (Kazazian et al. 1995. The Metabolic and Molecular Basis of Inherited Disease. In: Scriver, Beadet, Sly and Valle, Ed. New York, McGraw-Hill Inc. III: 3241-3267; incorporated herein by reference).

Haemophilia A is a sex-linked bleeding disorder characterized by a deficiency in Factor VIII. The disease occurs in about 0.01% of the male population. Haemophilia A can be treated by administering Factor VIII-containing blood plasma obtained from healthy donors. This treatment has several disadvantages, however. The supply of Factor VIII is limited and very expensive; the concentration of Factor VIII in blood is only about 100 ng/ml and the yields using current plasma fractionation methods are low. Since the source of Factor VIII is pooled donor blood, the recipient runs a high risk of acquiring various infectious diseases, including those caused by hepatitis non-A, non-B, hepatitis B or AIDS viruses which may be present in the donor blood. In addition, recipients may develop antibodies against the exogenous Factor VIII, some of which can greatly reduce its effectiveness.

As stated above, coagulation Factor VIII (FVIII) serves its role in the intrinsic coagulation pathway as a cofactor for activated Factor IX (FIXa) in the proteolytic activation of Factor X (for reviews, see Fay, P. J. (1999) Thromb. Haemostasis 82, 193-200; Lenting, P. J., van Mourik, J. A., and Mertens, K. (1998) Blood 92, 3983-3996; incorporated herein by reference). Factor VIII is a 300-kDa glycoprotein that comprises a discrete domain structure (A1-a1-A2-a2-B-a3-A3-C1-C2) (Lenting, P. J., van Mourik, J. A., and Mertens, K. (1998) Blood 92, 3983-3996; Vehar, G. A., Keyt, B., Eaton, D., Rodriguez, H., O'Brien, D. P., Rotblat, F., Opperman, H., Keck, R., Wood, W. I., Harkins, R. N., Tuddenham, E. G. D., Lawn, R. M., and Capon, D. J. (1984) Nature 312, 337-342; incorporated herein by reference). The A and C domains share 30-40% homology with the A and C domains of the structurally related protein Factor V, whereas the B domain and the short acidic regions a1, a2, and a3 are unique for FVIII (Church, W. R., Jernigan, R. L., Toole, J., Hewick, R. M., Knopf, J., Knutson, G. J., Nesheim, M. E., Mann, K. G., and Fass, D. N. (1984) Proc. Natl. Acad. Sci. U.S.A. 81, 6934-6937; incorporated herein by reference).

In plasma, FVIII circulates as a metal-ion-linked heterodimer consisting of a 90-220-kDa heavy chain (A1-a1-A2-a2-B) and an 80-kDa light chain (a3-A3-C1-C2) (Rotblat, F., O'Brien, D. P., O'Brien, F. J., Goodall, A. H., and Tuddenham, E. G. D. (1985) Biochemistry 24, 4294-4300; Kaufman, R. J., Wasly, L. C., and Dorner, A. J. (1988) J. Biol. Chem. 263, 6352-6362; incorporated herein by reference). The inactive protein is tightly associated with its carrier protein von Willebrand Factor (vWF) (Lollar, P., Hill-Eubanks, D. C., and Parker, C. G. (1988) J. Biol. Chem. 263, 10451-10455; incorporated herein by reference). Limited proteolysis by either thrombin or Factor Xa converts the FVIII precursor into its activated derivative (Lollar, P., Knutson, G. J., and Fass, D. N. (1985) Biochemistry 24, 8056-8064; Eaton, D., Rodriguez, H., and Vehar G. A. (1986) Biochemistry 25, 505-512; incorporated herein by reference). The B domain and the acidic region that borders the A3 domain are then removed from the molecule (Fay, P. J., Haidaris, P. J., and Smudzin, T. M. (1991) J. Biol. Chem. 266, 8957-8962; incorporated herein by reference), which leads to the loss of high affinity binding to vWF (Lollar, P., et al. (1988) supra). The resulting activated FVIII (FVIIIa) molecule consists of a heterotrimer comprising the A2-a2 domain that is non-covalently associated with the metal-ion-linked A1-a1/A3-C1-C2 moiety (Fay, P. J., et al. (1991) supra).

Within the heavy chain and light chain of FVIII, several regions are identified as FIXa interactive sites (Fay P. J., Beattie, T., Huggins, C. F., and Regan, L. M. (1994) J. Biol. Chem. 269, 20522-20527; Bajaj, S. P., Schmidt, A. E., Mathur, A., Padmanabhan, K., Zhong, D., Mastri, M., and Fay, P. J. (2001) J. Biol. Chem. 276, 16302-16309; Lenting, P. J., van de Loo, J. W. H. P., Donath, M. J., S., H., van Mourik, J., A., and Mertens, K. (1996) J. Biol. Chem. 271, 1935-1940; incorporated herein by reference). The A2 domain residues $Arg^{484}$-$Phe^{509}$, $Ser^{558}$-$Gln^{565}$, and $Arg^{698}$-$Asp^{712}$ contribute to binding of the heavy chain to FIXa (Fay P. J., (1994) supra; Bajaj., (2001) supra; Fay, P. J., and Scandella, D. (1999) J. Biol. Chem. 274, 29826-29830; incorporated herein by reference). Within the FVIII light chain, the A3 domain region $Glu^{1811}$-$Lys^{1818}$ has been identified as a FIXa interactive site (Lenting, P. J., (1996) supra). In addition, FVIII regions $Arg^{484}$-$Phe^{509}$ and $Lys^{1804}$-$Lys^{1818}$ have also been identified as target epitopes for antibodies that may occur in hemophilia patients. Such antibodies inhibit FVIII activity by interfering with the complex assembly of FVIIIa and activated FIX (Haeley, J. F., Lubin, 1. M., Nakai, H., Saenko, E. L., Hoyer, L. W., Scandella, D., and Lollar, P. (1995) J. Biol. Chem. 270, 14505-14509; Fijnvandraat, K., Celie, P. H. N., Turenhout, E. A. M., van Mourik, J. A., ten Cate, J. W., Mertens, K., Peters, M., and Voorberg, J. (1998) Blood 91, 2347-2352; Zhong, D., Saenko, E. L., Shima, M., Felch, M., and Scandella, D. (1998) Blood 92, 136-142; incorporated herein by reference).

The half-life of Factor VIII can be prolonged by influencing the mechanism of the Factor VIII degradation (clearance), for example, by reduction of the affinity of Factor VIII for the receptors which play a role in its clearance, either directly, by modification of Factor VIII at its binding site(s) for the relevant clearance receptor(s) or indirectly, by using compounds that influence the binding between Factor VIII and its receptors. Since the cellular receptors involved in said process and the molecular sites involved in Factor VIII-receptor interaction were not known, the production of such agents has been problematic.

The half-life of non-activated Factor VIII heterodimers is dependent on the existence of von Willebrand Factor which has a pronounced affinity for Factor VIII (but not for Factor VIIIa) and which serves as a carrier protein (Sadler, J. E. and Davie, E. W.: Haemophilia A, Haemophilia B and von Willebrand's Disease, in Stamatoyannopoulos, G. et al. (Eds.), The Molecular basis of blood diseases. W. B. Saunders Co., Philadelphia, 1987, page 576-602). It is known that patients who have von Willebrand's Disease type 3, who do not show any detectable von Willebrand Factor in their circulatory system, also have a secondary deficiency in Factor VIII. Furthermore, the half-life of intravenously administered Factor VIII in these patients is 2 to 4 hours, which is clearly shorter than the 10 to 40 hours which are reported for Haemophilia A patients.

These findings imply that Factor VIII tends to be rapidly cleared from the circulatory system and that this process is inhibited to a certain extent by complex formation with the natural carrier, von Willebrand Factor.

Recently, Factor VIII activated by thrombin has been implicated in binding to Low Density Lipoprotein Receptor Protein (hereinafter referred to as "LRP") (Yakhyaev, A. et al., Blood, vol. 90 (Suppl. 1), 1997, 126-I, incorporated herein by reference. The abstract of this document describes the cellular uptake and degradation of thrombin-activated Factor VIII fragments and reports that the A2 domain, but not the other two subunits of the Factor VIIIa heterotrimer, interacts with cellular LRP. The authors propose that the A2 domain binding to LRP further destabilizes the interaction between the A2 domain in the Factor VIIIa heterotrimer and that Factor VIIIa activity is thereby down-regulated.

It has also been demonstrated that non-activated FVIII interacts with the multifunctional endocytic receptor low-density lipoprotein receptor-related protein (LRP) (Lenting, P. J., Neels, J. G., van den Berg, B. M. M., Clijsters, P. P. F. M., Meijerman, D. W. E., Pannekoek, H., van Mourik, J. A., Mertens, K., and van Zonneveld, A.,-J. (1999) J. Biol. Chem. 274, 23734-23739; WO 00/28021; Saenko, E. L., Yakhyaev, A. V., Mikhailenko, I., Strickland, D. K., and Sarafanov, A. G. (1999) J. Biol. Chem. 274, 37685-37692; incorporated herein by reference). It is suggested that this receptor plays a role in the clearance of FVIII from the circulation (Saenko, E. L., et al, supra; Schwarz, H. P., Lenting, P. J., Binder, B., Mihaly, J., Denis, C., Dorner, F., and Turecek, P. L. (2000) Blood 95, 1703-1708; incorporated herein by reference).

LRP is a member of the low-density lipoprotein (LDL) receptor family that also includes LDL receptor, very low-density lipoprotein receptor, a polipoprotein E receptor 2, and megalin (for reviews see Neels J. G., Horn, I. R., van den Berg, B. M. M., Pannekoek, H., and van Zonneveld, A.-J. (1998) Fibrinolysis Proteolysis 12, 219-240; Herz, J., and Strickland, D. K. (2001) J. Clin. Invest. 108, 779-784; incorporated herein by reference). It is expressed in a variety of tissues, including liver, lung, placenta, and brain (Moestrup, S. K., Gliemann, J., and Pallesen, G. (1992) Cell Tissue Res. 269, 375-382; incorporated herein by reference). The receptor consists of an extracellular 515-kDa α-chain, which is non-covalently linked to a transmembrane 85-kDa β-chain (Herz, J., Kowal, R. C., Goldstein, J. L., and Brown, M. S. (1990) EMBO J. 9, 1769-1776; incorporated herein by reference). The α-chain contains four clusters of a varying number of complement-type repeats that mediate the binding of many structurally and functionally unrelated ligands (Moestrup, S. K., Hotlet, T. L., Etzerodt, M., Thogersen, H. C., Nykjaer, A., Andreasen, P. A., Rasmussen, H. H., Sottrup-Jensen, L., and Gliemann, J. (1993) J. Biol. Chem. 268, 13691-13696; Willnow, T. E., Orth, K., and Herz, J. (1994) J. Biol. Chem. 269, 15827-15832; Neels, J. G., van den Berg, B. M. M., Lookene, A., Olivecrona, G., Pannekoek, H., and van Zonneveld, A.-J. (1999) J. Biol. Chem. 274, 31305-31311; incorporated herein by reference).

The β-chain comprises a trans-membrane domain and a short cytoplasmatic tail which is essential for endocytosis. The alpha chain functions as a large ectodomain and comprises three types of repeats: epidermic growth-Factor-like domains, Tyr-Trp-Thr-Asp sequences and LDL-receptor-class A domains. These class A domains, which have been implicated in ligand binding, are present in four separate clusters which are called Cluster I (2 domains), Cluster II (8 domains), Cluster III (10 domains) and Cluster IV (11 domains).

LRP is also expressed in cell-types like monkey kidney cells (COS) or Chinese hamster ovary cells (CHO) FitzGerald, D. J., et al., J. Cell Biol. Vol. 129, 1995, pages 1533-1541; incorporated herein by reference) which are those often used for the expression of mammalian proteins, including Factor VIII (Kaufman, R. J. et al., Blood, Coag. Fibrinol, vol. 8 (Suppl. 2), 1997, pages 3-14; incorporated herein by reference).

LRP plays a role in the clearance of a multitude of ligands, including proteases, inhibitors of the Kunitz type, protease-serpin complexes, lipases and lipoproteins which implicates that LRP plays an important role in several physiological and pathophysiological clearance processes (Narita et al., Blood, vol. 2, pages 555-560, 1998; Orth et al., Proc. Natl. Acad. Sci., vol. 89, pages 7422-7426, 1992; Kounnas et al., J. Biol. Chem., vol. 271, page 6523-6529, 1996; incorporated herein by reference).

LRP also binds the activated, non-enzymatic cofactor Factor VIIIa (Yakhyaev, A. et al., Blood, vol. 90, (Suppl. 1), 1997, 126-I). While this disclosure implicates LRP in Factor VIIIa regulation, there is no hint of a role for LRP in the regulation of non-activated heterodimer Factor VIII.

FVIII light chain has been demonstrated to interact with recombinant LRP clusters II and IV, whereas no binding was observed to LRP clusters I and III (Neels, J. G., et al (1999) supra).

Several attempts to modify several regions of the Factor VIII polypeptide have been carried out to improve the pharmaco-kinetic profile of Factor VIII:

WO 87/07144 describes several modifications of proteolytic cleavage sites, which comprise arginine and lysine residues, to reduce the lability of the molecule for a specific protease catalyzed cleavage, for example Factor Xa-cleavage site between $Arg^{1721}$ and $Ala^{1722}$.

WO 95/18827, WO 95/18828 and WO 95/18829 describe Factor VIII derivatives with modifications in the A2 regions of the heavy chain.

WO 97/03193 discloses a Factor VIII polypeptide analogues, wherein the modifications alter the metal binding characteristics of the molecule.

In WO 97/03195, Factor VIII:C polypeptide analogues are described wherein modifications in one or more amino acid residues that are located adjacent to an Arg residue are provided.

EP 808 901 describes the construction of Factor VIII variants with at least one mutation in at least one immunodominant region of Factor VIII and use of this Factor VIII variant for the treatment of patients with Factor VIII inhibitors. These modifications do not lead to a prolonged half-life or increased stability of the Factor VIII variant in vivo or in vitro.

Furthermore, WO 00/28021 describes a Factor VIII polypeptide with a Factor VIII:C activity which has modifications in the A3 and/or C1 or C2 domain of the light chain and which is characterized in that the modification influences binding affinity to low-density lipoprotein receptor protein (LRP).

Molecular cloning of Factor VIII cDNA obtained from human mRNA and the subsequent production of proteins with Factor VIII activity in mammalian, yeast and bacterial cells has been reported (see WO 85/01961, EP 160 457, EP 150 735 and EP 253 455; incorporated herein by reference). A method for producing proteins with Factor VIII activity using transformed microorganisms is disclosed in EP 253 455; incorporated herein by reference. European patent applications EP 150 735 and EP 123 945 and Brinkhous et al. (1985) disclose Factor VIII activity in proteolytic cleavage products of Factor VIII (incorporated herein by reference). A complex of two proteolytic cleavage products of Factor VIII, a 92 kDa and an 80 kDa polypeptide exhibits enhanced Factor VIII activity. (Fay et al., Biochem. Biophys. Acta (1986) 871:268-278; Faton et al., Biochemistry (1986) 25:505-512; incorporated herein by reference).

Thus, the inventors set out to make Factor VIII preparations available that increase stability and half-life of Factor VIII in vitro and in vivo.

SUMMARY OF THE INVENTION

Surprisingly, the inventors have discovered that specific peptides comprising partial Factor VIII amino acid sequences as well as antibodies directed against specific epitopes within these peptides are capable of significantly improving the stability of Factor VIII in vitro and in vivo.

Hence, the present invention generally concerns the use of peptides derived from and antibodies generated against Factor VIII and the inhibition of Factor VIII interaction with LRP. Furthermore, the present invention concerns a method to inhibit LRP interaction with Factor VIII as well as a method to decrease Factor VIII degradation and/or prolong Factor VIII half-life in a biological fluid and/or a method to treat patients suffering from a blood coagulation disorder, especially Haemophilia A. The present invention also concerns a pharmaceutical composition useful for the decrease of Factor VIII degradation in a biological fluid, the inhibition of Factor VIII interaction with LRP, and/or the prolongation of Factor VIII half-life in a biological fluid for treatment of a blood coagulation disorder, especially Haemophilia A.

DETAILED DESCRIPTION OF THE DRAWINGS

FIG. 1. Binding of FVIII light chain fragments to immobilized LRP. LRP immobilized at a CM5 sensor-chip at 16 fmol/mm$^2$ was incubated with: A, FVIII light chain (150 nM) (solid line) and Factor Xa-cleaved light chain (150 nM) (dotted line). B, a3-A3-C1 fragment (150 nM) (solid line) and isolated C2 domain (750 nM) (dotted line). Incubations were performed in 150 mM NaCl, 2 mM CaCl$_2$, 0.005% (v/v) Tween® 20, and 20 mM Hepes (pH 7.4) at a flow rate of 20 µl/min for 2 min at 25° C. Dissociation was initiated upon replacement of ligand solution by buffer. Response is indicated as Resonance Units (RU) and is corrected for nonspecific binding, which was less than 5% relative to LRP-coated channels.

Figure 2:
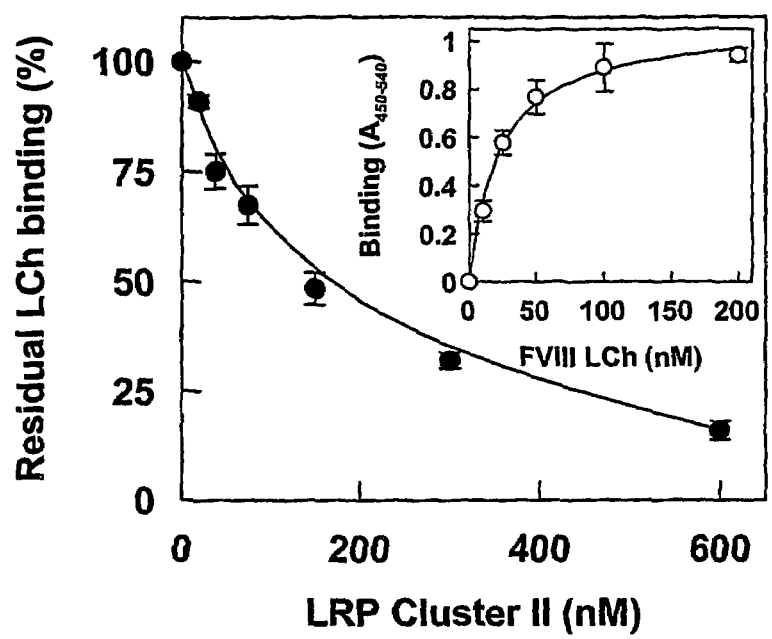

FIG. 2. Binding of FVIII light chain to recombinant LRP fragments. FVIII light chain (LCh) (25 nM) was incubated with immobilized LRP cluster IV (1 pmol/well) in a volume of 50 µl in 150 mM NaCl, 5 mM CaCl$_2$, 1% (w/v) HSA, 0.1% Tween® 20, and 50 mM Tris (pH 7.4) in the presence or absence of various concentrations of recombinant LRP cluster II (0-600 nM) for 2 h at 37° C. After washing with the same buffer, bound FVIII light chain was quantified by incubation with peroxidase-conjugated anti-FVIII antibody CLB-CAg 12 for 15 min at 37° C. Residual binding is expressed as the percentage of binding in the absence of competitor and is corrected for nonspecific binding (less than 5% relative to binding to LRP cluster II-immobilized wells). Inset, serial dilutions of FVIII light chain were incubated with immobilized LRP cluster II (1 pmol/well) in a volume of 50 µl in 150 mM NaCl, 5 mM CaCl$_2$, 1% (w/v) HSA, 0.1% Tween® 20, and 50 mM Tris (pH 7.4) for 2 h at 37° C. After washing with the same buffer, bound FVIII light chain was quantfied as described above. Data represent the mean±S.D. of three experiments FIG. 3. Binding of LRP cluster II to immobilized FVa light chain. LRP Cluster II (100 nM) was incubated with either immobilized FVIII light chain (71 fmol/mm$^2$) (I) or FVa light chain (76 fmol/mm$^2$) (II) in 150 mM NaCl, 2 mM CaCl$_2$, 0.005% (v/v) Tween® 20, and 20 mM Hepes (pH 7.4) at a flow rate of 20 µl/min for 2 min at 25° C. Response is indicated as Resonance Units (RU) and is corrected for nonspecific binding, which was less than 5% relative to coated channels.

Figure 4:
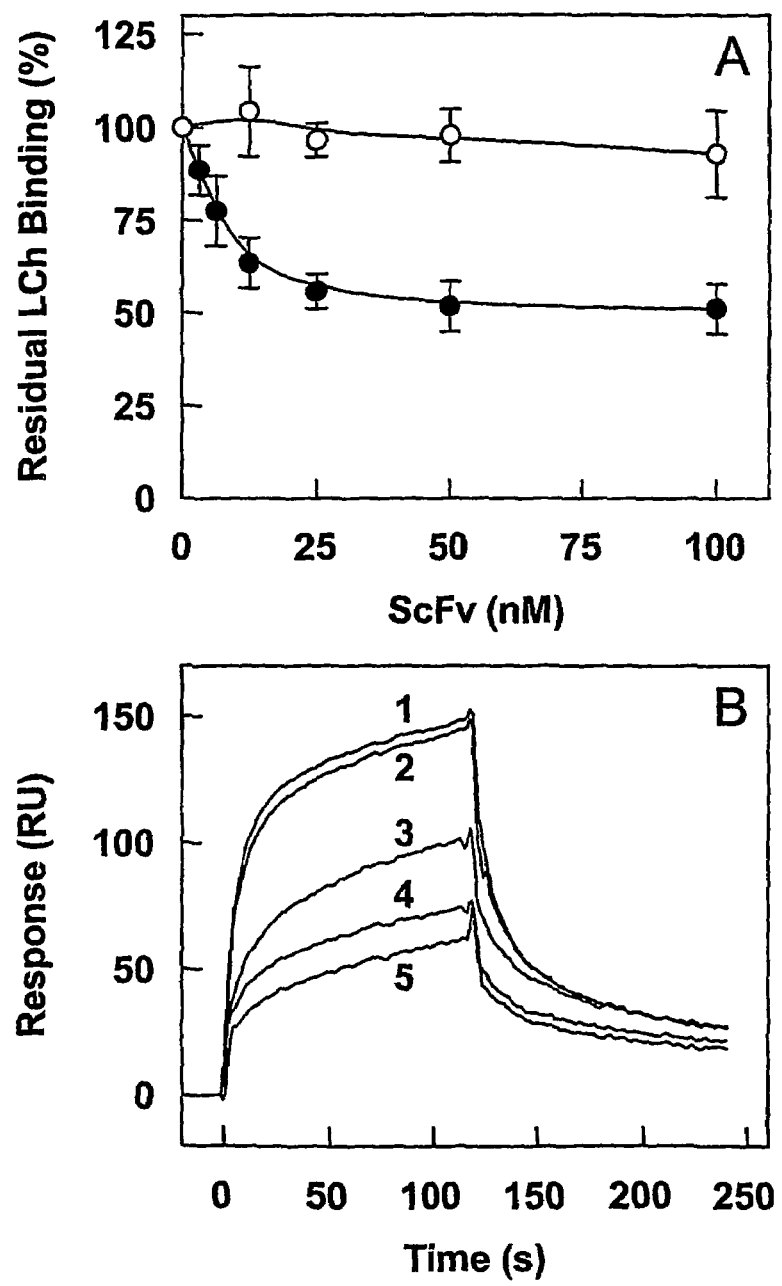

FIG. 4. Effect of scFv antibody fragments on the interaction between FVIII light chain and LRP. A, FVIII light chain (LCh) (25 nM) was incubated with immobilized LRP cluster II (1 pmol/well) in a volume of 50 µl in 150 mM NaCl, 5 mM CaCl$_2$, 1% (w/v) HSA, 0.1% Tween® 20, and 50 mM Tris (pH 7.4) in the presence of various concentrations (0-100 nM) of scFv KM41 (closed circles) or scFv KM36 (open circles) for 2 h at 37° C. After washing with the same buffer, bound FVIII light chain was quantified by incubation with peroxidase-conjugated anti-FVIII antibody CLB-CAg 12 for 15 min at 37° C. Residual binding is expressed as the percentage of binding in the absence of competitor and is corrected for nonspecific binding (less than 5% relative to binding to LRP cluster II-immobilized wells). Data represent the mean±S.D. of three experiments. B, FVIII light chain (50 nM) was incubated with immobilized LRP (16 fmol/mm$^2$) as described in the legend of FIG. 1. Binding was assessed in the absence (curve 1) or in the presence of increasing concentrations of scFv KM41 (20, 60, 300, 500 nM, curves 2-5, respectively). Complexes were allowed to form for 30 min before SPR analysis.

Figure 5:
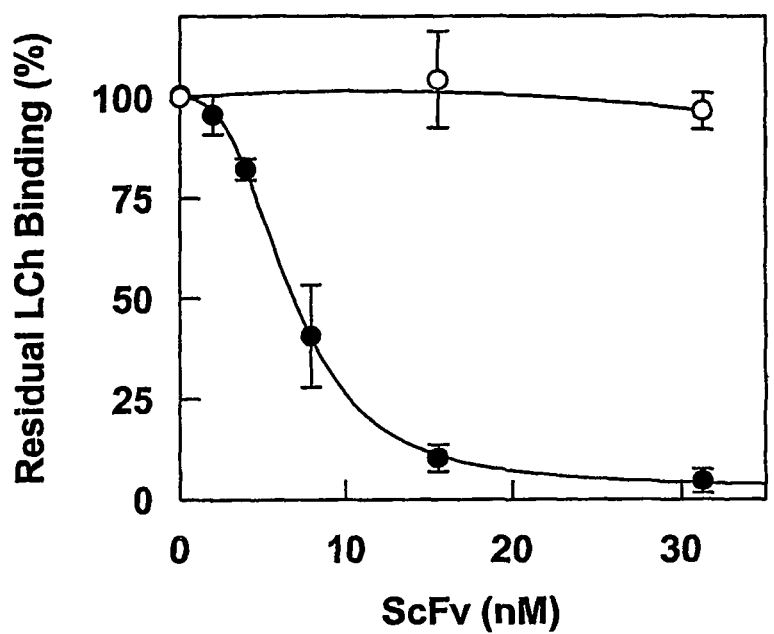

FIG. 5. Effect of scFv KM33 on the interaction between FVIII light chain and LRP. FVIII light chain (LCh) (25 nM) was incubated with immobilized LRP cluster II (1 pmol/well) in a volume of 50 µl in 150 mM NaCl, 5 mM CaCl$_2$, 1% (w/v) HSA, 0.1% Tween® 20, and 50 mM Tris (pH 7.4) in the presence of various concentrations (0-30 nM) of scFv KM36 (open circles) or scFv KM33 (closed circles) for 2 h at 37° C. After washing with the same buffer, bound FVIII Light chain was quantified by incubation with peroxidase-conjugated anti-FVIII antibody CLB-CAg 12 for 15 min at 37° C. Residual binding is expressed as the percentage of binding in the absence of competitor and is corrected for nonspecific binding (less than 5% relative to binding to cluster-coated wells). Data represent the mean±S.D. of three experiments.

Figure 6:
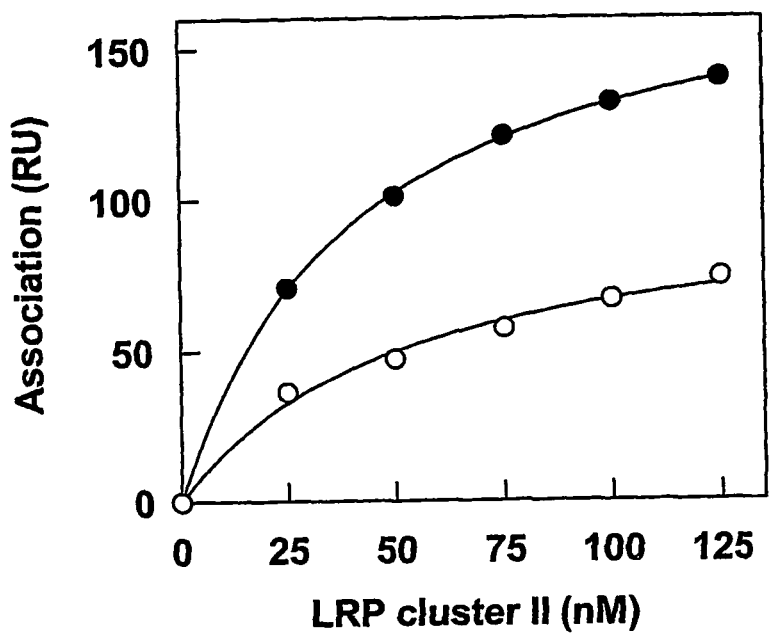

FIG. 6. Binding of LRP cluster II to the FVIII/FV$^{1811-1818}$ light chain chimera. ScFv EL14 at a CM5 sensor chip (67 fmol/mm$^2$) was incubated with either the recombinant wild-type FVIII light chain or the recombinant FVIII/FV$^{1811-1818}$ chimera till a density of 20 fmol/mm$^2$, in 150 mM NaCl, 50 mM Tris (pH 7.4). LRP cluster II (25-125 nM) was passed over two separate channels with immobilized FVIII/FV$^{1811-1818}$ chimera (open circles) or intact FVIII light chain (closed circles), respectively, and one control (scFv EL14-coated) channel in 150 mM NaCl, 2 mM CaCl$_2$, 0.005% (v/v) Tween® 20, and 20 mM Hepes (pH 7.4) for 2 min at a flow rate of 20 µl/min at 25° C. Bound LRP cluster II is expressed as the amount associated after 2 min.

Figure 7:
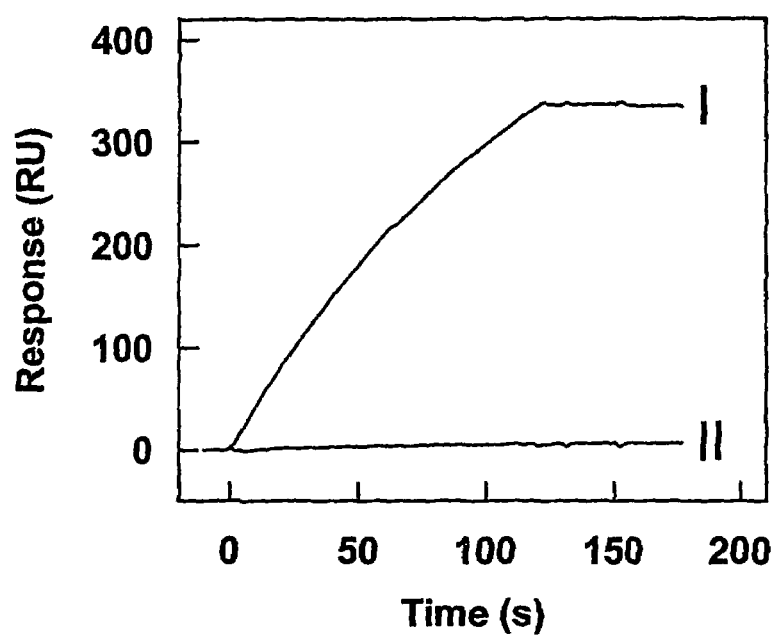

FIG. 7. Binding of scFv KM41 to the FVIII/FV$^{1811-1818}$ light chain chimera. ScFv EL14 at a CM5 sensor chip (67 fmol/mm$^2$) was incubated with either the recombinant wild-type FVIII light chain or the recombinant FVIII/FV$^{1811-1818}$ chimera till a density of 20 fmol/mm$^2$, in 150 mM NaCl, 50 mM Tris (pH 7.4). ScFv KM41 (40 nM) was passed over two separate channels with immobilized intact FVIII light chain (I) or FVIII/FV$^{1811-1818}$ chimera (II), respectively. Response is indicated as Resonance Units (RU) and is corrected for nonspecific binding.

Figure 8:
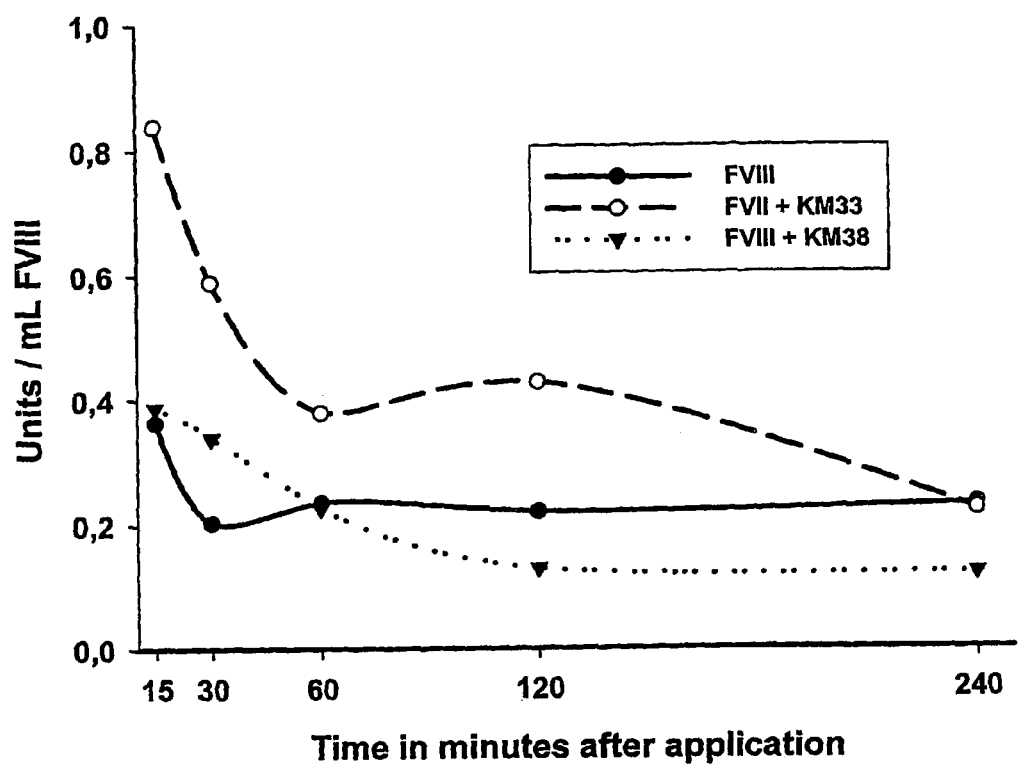

FIG. 8. According to Example II, mice were injected either with human FVIII alone, human FVIII in the presence of a control scFv-fragment (KM38) and with human FVIII in the presence of a scFv-fragment (KM33) specifically interfering with the putative FVIII-LRP interaction.

DETAILED DESCRIPTION OF THE INVENTION

One embodiment of the invention relates to the use of a peptide comprising an amino acid sequence as defined in any of SEQ ID Nos. 1, 2, 3 or 4 as derived from Factor VIII but not having any substantial Factor VIII activity to inhibit Factor VIII interaction with LRP.

The term "peptide" relates to a molecule that is comprised of a sequence of amino acids joined via peptide bonds. Preferably, the peptides useful for the invention are comprised of those 20 amino acids that are commonly found in proteins (see for example, the well-known textbook "Biochemistry" by A. Lehninger, 2$^{nd}$ Ed., Worth Publishers, N.Y., N.Y. (1975).

A peptide useful for the present invention can also be a derivative of a peptide comprising an amino acid sequence as defined in any of SEQ ID Nos. 1, 2, 3 or 4, as derived from Factor VIII but not having any substantial Factor VIII activity, modified such that its amino acid sequence comprises one or more deletions, additions, substitutions and/or inversions that do not significantly alter the ability of said peptide to reduce the interaction between Factor VIII and LRP proteins.

When a peptide useful for the present invention contains one or amino acid substitution(s), it is preferable that said one or more amino acid substitution(s) are conservative amino acid substitutions. For example, if a substitution occurs in a non-polar hydrophobic amino acid such as alanine, leucine, isoleucine, valine, proline, phenylalanine, tryptophan and methionine, then it is preferable that the substituted amino acid is selected from a non-polar hydrophobic amino acid such as alanine, leucine, isoleucine, valine, proline, phenylalanine, tryptophan and methionine. Likewise, if a substitution occurs in an uncharged polar amino acid such as serine, threonine, tyrosine, asparagine, glutamine, cysteine or glycine, then it is preferable that the substituted amino acid is selected from an uncharged polar amino acid such as serine, threonine, tyrosine, asparagine, glutamine, cysteine or glycine. If a substitution occurs in a positively charged (basic) amino acid such as lysine, arginine or histidine, then it is preferable that the substituted amino acid is selected from a positively charged (basic) amino acid such as lysine, arginine or histidine. Likewise, if a substitution occurs in a negatively charged (acidic) amino acid such as aspartic acid or glutamic acid, then it is preferable that the substituted amino acid is selected from a negatively charged (acidic) amino acid such as aspartic acid or glutamic acid. The peptide useful for the invention can be composed of D-amino acids, L-amino acids or a mixture of D- and L-amino acids.

A peptide useful for the present invention also embraces multimeric forms of any of the peptides as defined in SEQ ID Nos. 1, 2, 3 or 4, such as e.g. tandem or alternating repeats of one or more of these peptides.

Chemical modifications of particular amino acids of said peptides are also embraced, especially chemical modifications of the N-terminal and/or C-terminal amino acid residues, that block the terminal amino and/or carboxy groups and may increase the stability of said peptides against degradation in vitro or in vivo, or that add a molecule or moiety to the peptide having a function, such as a carrier function (including albumin or other plasma proteins), a targeting function or modify solubility of the peptides. The term "modification" further embraces the addition or removal of glycosyl-residues.

Peptides useful for the present invention may be produced in whole or in part by standard peptide synthesis techniques or by recombinant DNA techniques.

One particular peptide useful for the invention comprises the amino acid sequence of SEQ ID NO:1 (Glu$^{1811}$-Lys$^{1818}$). Further particular peptides useful for the invention comprises the amino acid sequences from SEQ ID NO:2 (Lys$^{1804}$-Lys$^{1818}$) or SEQ ID NO:3 (Tyr$^{1815}$-Ala$^{1834}$). Thus, a further peptide useful for the invention comprises the amino acid sequence Lys$^{1804}$-Ala$^{1834}$ (SEQ ID NO:4).

Preferably, a peptide useful for the present invention has less that 5.0% of the Factor VIII activity, more preferably less than 1.0% of the Factor VIII activity, and most preferably essentially no activity, as compared to the corresponding Factor VIII activity of the naturally occurring Factor VIII molecule from which said peptide of the present invention was derived as measured in one of the above-mentioned assays for Factor VIII activity.

The evaluation of Factor VIII activity can be carried out by means of a suitable assay, in particular with any assay that is typically performed to determine Factor VIII activity in samples, such as the one-step clot assay as described in Mikaelsson and Oswaldson, Scan. J. Hematol. Suppl. 33, 79-86, 1984, for example or a chromogenic assay such as Factor VIII IMMUNOCHROM (Baxter).

Factor VIII activity can also be performed by measuring the ability of Factor VIII to act as a cofactor for Factor IXa in the conversion of Factor X to Factor Xa, whereby a chromogenic substrate is used for Factor Xa (Coatest Factor VIII, Chomogenix, Moelndal, Sweden).

A further embodiment of the invention relates to the use of an antibody, which specifically binds to one or more epitopes within a peptide comprising an amino acid sequence as defined in any of SEQ ID Nos. 1, 2, 3 or 4 as derived from Factor VIII but not having any substantial Factor VIII activity, to inhibit Factor VIII interaction with LRP.

The term "antibody" as used herein is meant to include a polyclonal or monoclonal antibody, preferably monoclonal antibody, and fragments or regions thereof as well as derivatives thereof that are capable of specifically binding to one or more epitopes within Factor VIII or a peptide useful for the present invention and interfering with the interaction between a Factor VIII molecule and a Low Density Lipoprotein Receptor-related Protein (LRP).

The term "epitope" as used herein is meant to refer to the whole or part of a peptide useful for the present invention that mimics the 1°, 2° and/or 3° structure of all or part of the corresponding amino acids found in Factor VIII and that is capable of being specifically recognized by an antibody that inhibits the interaction between Factor VIII and LRP. An epitope may comprise the peptide sequence per se, i.e. the 1° structure of the peptide, the peptide in various three dimensional conformations, i.e. the 2° or 3° structure of the peptide sequence and/or modifications to the amino acids of said peptides such as the addition of sugar molecules, e.g. glycosylated peptides. Without being bound by any particular theory or biological mechanism of action, it is possible that the peptides useful for practicing the present invention comprise at least two different epitopes. One epitope seems to be a primary amino acid sequence located within SEQ ID NO:1 ($Gly^{1811}$-$Lys^{1818}$). The other epitope may be comprised of a combination of the amino acid sequences located adjacent to the above primary epitope; i.e. the other epitope may be formed from SEQ ID NO:2 ($Lys^{1804}$-$Lys^{1818}$) and/or SEQ ID NO:3 ($Tyr^{1815}$-$Ala^{1834}$). This epitope may also be a secondary or tertiary structure epitope and may comprise both of the amino acid sequences $Lys^{1804}$-$Lys^{1818}$ and $Tyr^{1815}$-$Ala^{1834}$.

Fragments of antibodies include, for example, Fab, Fab', $F(ab')_2$, Fv and scFv fragments. These fragments can be produced from intact antibodies using methods that are well known in the art, for example by proteolytic cleavage with enzymes such as papain to produce Fab fragments, or pepsin to produce $F(ab')_2$ fragments.

In one preferred embodiment, the antibody useful for the practice of the invention is a scFv antibody fragment. Preferably, the antibody comprises the amino acid sequence of the antibody as described in the examples as KM33 (see SEQ ID NO:20 for the amino acid sequence of the heavy chain of KM33, SEQ ID NO:22 for the amino acid sequence of the light chain of KM33 and SEQ ID NO:26 for a fusion protein comprising the light and heavy chains of KM33 joined by a peptide linker) and/or as provided by the GenBank Accession Number AF234247 (VHKM33) or the antibody as described in the examples as KM41 (see SEQ ID NO:16 for the amino acid sequence of the heavy chain of KM41, SEQ ID NO:18 for the amino acid sequence of the light chain of KM41 and SEQ ID NO:25 for a fusion protein comprising the light and heavy chains of KM41 joined by a peptide linker) and/or as provided by the GenBank Accession Number AF234258 (VLKM41).

These and other scFvs can be produced as described in van der Brink, E. N. et al, Blood 97(4), 966-972 (2001) (hereby incorporated by reference).

Preferably, an antibody useful for the invention is capable of inhibiting the interaction between Factor VIII and Low Density Lipoprotein Receptor-related Protein (LRP) such that this interaction is reduced by at least 20%, more preferably at least 50%, still more preferably at least 90% or 95% or more, as compared to the interaction, for example, between Factor VIII and LRP derived from a given source.

The interaction between Factor VIII and LRP can be determined using the Surface Plasmon Resonance or solid-phase binding assays as described herein.

As used herein, the term "Low Density Lipoprotein Receptor-related Protein" is abbreviated as "LRP" and these terms are used interchangeably to refer to the a membrane glycoprotein that is a member of the low density lipoprotein (LDL) receptor family of proteins (see Gliemann, J. in Biol. Chem. 379, 951-964 (1998; incorporated by reference). Human LRP contains 31 class A cysteine-rich repeat (known as LDLRA) domains which are distributed in the LRP molecule in four clusters known as clusters I, II, III and IV. Cluster II comprises a domain known as CL-II-1/2 that spans the amino-terminal flanking epidermal growth Factor repeat E4 and the LDLRA domains C3-C7. This CL-II-1/2 domain interacts with Factor VIII (see Neels, J. G. et al., supra).

The present invention also relates to a pharmaceutical composition that comprises at least one peptide wherein said peptide comprises the amino acid sequence as defined in any of SEQ ID Nos. 1, 2, 3 or 4 as derived from Factor VIII, but not having any substantial Factor VIII activity, or an antibody which specifically binds to one or more epitopes within said amino acid sequences, and a physiologically acceptable excipient, carrier, diluent and/or stabilizator.

Pharmaceutical compositions according to the invention can comprise one or more peptides useful for the present invention or one or more antibodies useful for the invention or derivatives thereof. Pharmaceutical compositions according to the invention can also comprise one of more further therapeutic or prophylactic active ingredients. In one embodiment, the pharmaceutical composition comprises one or more peptides useful for the present invention. In another embodiment, the pharmaceutical composition comprises or one or more antibodies useful for the invention directed against said peptides. When the pharmaceutical composition comprises one or more antibodies useful for the invention, said pharmaceutical composition may further contain Factor VIII. The Factor VIII in such a pharmaceutical composition can be derived from any naturally occurring, synthetic or recombinant source.

A peptide and/or antibody useful for the invention can be formulated as a solution, suspension, emulsion, or lyophilised powder in association with a pharmaceutically acceptable vehicle such as one or more excipient(s), carrier(s), diluent(s) and stabilizer(s). Suitable carriers include, but are not limited to, diluents or fillers, sterile aqueous media and various non-toxic organic solvents. Examples of such vehicles are water, saline, Ringer's solution, dextrose solutions, and human serum albumin solutions. Liposomes and non-aqueous vehicles such as fixed oils may also be used. The vehicle or lyophilizate may contain additives that maintain the isotonicity, for example, NaCl, sucrose, mannitol, and stability, for example buffers and/or preservatives. Suitable pharmaceutically acceptable vehicles are described in Remington's Pharmaceutical Sciences by A. Osol, a standard textbook in this field (incorporated by reference). The compositions may be formulated in the form of tablets, capsules, powders, aqueous suspensions or solutions, injectable solutions and the like.

Preferably, the pharmaceutical composition according to the invention is lyophilised.

The administration of the pharmaceutical composition according to the invention method of this invention should preferably be carried out employing a dosage regimen that ensures maximum therapeutic response until improvement is achieved. In general, the dose will be dependent on the molecular size of the peptide used. For a peptide of about 15 amino acids, the dosage for intravenous administration may vary between approximately 0.1 and 1000 mg/kg, preferably between 1 and 500 mg/kg, and most preferably between 10 and 100 mg/kg. For larger peptides, the dose may be increased accordingly. For oral administration, the dose may be substantially higher, bearing in mind, of course, that appropriate dosage may also be dependent on the patient's general health, age and other factors that may influence the response to the drug. The drug may be administered by continuous infusion, or at regular intervals of approximately 4 to 50 hours to maintain the therapeutic effect at the desired level.

The pharmaceutical composition according to the invention can be in the form of a single component preparation or can exist in combination with one or more other components in a kit.

The pharmaceutical composition according to the invention is intended for administration to mammals, preferably humans. When a peptide useful for the present invention is intended for administration to a particular mammal, for example a human, then it is preferred that said peptide is derived from that particular mammal. When the antibody useful for the invention is intended for administration to a particular mammal, for example a human, then it is preferred that said antibody was generated using an epitope derived from that particular mammal. In addition, it is preferable that an antibody useful for the invention that is intended for administration to a human is a human or humanized antibody.

A peptide useful for the present invention, an antibody useful for the invention as well as derivatives of these and pharmaceutical compositions comprising said peptides, antibodies and derivatives can be administered to a subject by any means that enables said peptide, antibody or derivatives thereof to reach the site of action in the body. Preferably, said peptides, antibodies and derivatives thereof and pharmaceutical compositions comprising said peptides, antibodies and derivatives thereof according to the invention are administered parenterally, i.e. intravenously, subcutaneously, or intramuscularly.

The pharmaceutical preparation according to the invention can be used to treat any subject in need of the administration of an agent that inhibits Factor VIII interaction with LRP, decreases Factor VIII degradation or prolongs Factor VIII half-life, in particular for the prevention or treatment of patients that have a blood coagulation disorder. Such a blood coagulation disorder can be at least in part caused by a deficiency, for example a genetic or inborn deficiency or an acquired deficiency, in Factor VIII. Such a blood coagulation disorder can also be at least in part caused by a deficiency, for example a genetic or inborn deficiency or an acquired deficiency, in any other protein involved in the coagulation pathway, including Factor IX, Factor V, Factor X or von Willebrand Factor. Preferably, said blood coagulation disorder is Haemophilia A or von Willebrand's disease.

Thus, the present invention further relates to the use of a peptide comprising an amino acid as defined in any of SEQ ID No. 1, 2, 3 or 4 as derived from Factor VIII, but not having any substantial Factor VIII activity, or of an antibody which specifically binds to one or more epitopes within said amino acid sequences for the preparation of a medicament for the treatment of a blood coagulation disorder.

In a preferred embodiment, the blood coagulation disorder is haemophilia A or von Willebrand's disease.

The pharmaceutical preparation according to the invention can also be used for the prevention or treatment of patients that have temporary impairment of their thrombolytic or fibrinolytic systems, for example, for patients directly before, during or after an operation or surgical procedure.

The present invention also relates to the use of a peptide comprising an amino acid sequence as defined in any of SEQ ID Nos. 1, 2, 3 or 4 as derived from Factor VIII, but not having any substantial Factor VIII activity, or an antibody which specifically binds to one or more epitopes within said amino acid sequences to decrease Factor VIII degradation in a biological fluid.

In a further related embodiment, the present invention provides a method to decrease Factor VIII degradation in a biological fluid, wherein a peptide as defined in any of SEQ ID Nos. 1, 2, 3 or 4 as derived from Factor VIII, but not having any substantial Factor VIII activity, or an antibody which specifically binds to one or more epitopes within said amino acid sequences is added to said biological fluid.

A "biological fluid" as used herein includes a fluid isolated from a mammal, such as blood, or a fraction thereof, such as plasma or serum, as well as the medium or fractions thereof obtained from the culture of eukaryotic or prokaryotic cells, cell lines or tissues.

Preferably, an amount of said peptide or said antibody is added which is sufficient to decrease Factor VIII degradation by at least 10%, more preferably by at least 20%, still more preferably by at least 50% and most preferably by essentially 100%.

The present invention further relates to the use, and related method, of a peptide comprising an amino acid sequence as defined in any of SEQ ID Nos. 1, 2, 3 or 4 as derived from Factor VIII, but not having any substantial Factor VIII activity, or of an antibody which specifically binds to one or more epitopes within said amino acid sequences to prolong Factor VIII half-life in a biological fluid.

Preferably, an amount of said peptide or said antibody is added which is sufficient to prolong Factor VIII half-life in a biological fluid at least 2-fold, more preferably at least 5-fold, and most preferably at least 10-fold.

The present invention further relates to the use, and the related method, of a peptide as defined in any of SEQ ID Nos. 1, 2, 3 or 4 as derived from Factor VIII, but not having any substantial Factor VIII activity, or an antibody which specifically binds to one or more epitopes within said amino acid sequences to inhibit the interaction of Factor VIII with LRP in a biological fluid. Preferably, an amount of said peptide or said antibody is added which is sufficient to achieve an inhibition extent of Factor VIII to with LRP of at least 10%, preferably at least 20%, most preferably at least 50%.

The present invention further relates to a method of treating a patient suffering from a blood coagulation disorder wherein said method comprises administering to said patient an effective amount of a peptide as defined in any of SEQ ID Nos. 1, 2, 3 or 4 as derived from Factor VIII, but not having any substantial Factor VIII activity, or an antibody which specifically binds to one or more epitopes within said amino acid sequences to inhibit the interaction of Factor VIII with LRP or a pharmaceutical composition comprising one or more of said peptide or one or more of said antibody.

The invention is illustrated in the subsequently described Examples, without intending that the invention be limited thereto.

EXAMPLE I

Materials—

CNBr-Sepharose 4B was from Amersham Pharmacia Biotech. Microtiter plates (Maxisorp), cell culture flasks, Optimem I medium, fetal calf serum (FCS), penicillin, and streptomycin were from Life Technologies (Life Technologies Inc., Breda, The Netherlands). Grace's Insect medium (TNM-FH) and Insect-XPRESS medium were purchased from BioWhiftaker (Alkmaar, The Netherlands).

Proteins—

Plasma-derived FVIII light chain and its Factor Xa-cleaved derivative were prepared as described previously (Lenting, P. J., Donath, M. J. S. H., van Mourik, J. A., and Mertens, K. (1994) J. Biol. Chem. 269, 7150-7155; Donath, M. S. J. H., Lenting, P. J., van Mourik, J. A., and Mertens, K. (1995) J. Biol. Chem. 270, 3648-3655; incorporated herein by reference). Anti-FVIII monoclonal antibodies CLB-CAg A, CLB-CAg 117 and CLB-CAg 12 have been described previously (Lenting, P. J. et al., (1994), supra; Leyte, A., Mertens, K., Distel, B., Evers, R. F., de Keyzer-Nellen, M. J., Groenen-van Dooren, M. M., de Bruin, J., Pannekoek, H., van Mourik, J. A., and Verbeet, M. P. (1989) Biochem. J. 263, 187-194; incorporated herein by reference). The anti-FVa light chain monoclonal antibody CLB-FV 5 was obtained by standard hybridoma techniques.

Single-chain domain variable antibody fragments (scFvs) directed against the light chain of FVIII were expressed in *Escherichia coli* strain TG1 and purified by metal-chelate chromatography (Qiagen, Hilden, Germany) as described previously (32-34), with the exception that scFvs KM36, KM41, and KM33 were eluted in 150 mM NaCl, 5 mM $CaCl_2$, 100 mM Imidazole, and 20 mM Hepes (pH 7.4).

Synthetic peptides encompassing the human FVIII regions $Trp^{1707}$-$Arg^{1721}$ (WDYGMSSSPHVLRNR) (SEQ ID NO:5), $Lys^{1804}$-$Lys^{1818}$ (KNFVKPNETKTYFWK) (SEQ ID NO:2), $Tyr^{1815}$-$Ala^{1834}$ (YFWKVQHHMAPTKDEFDCKA) (SEQ ID NO:3), $His^{1822}$-$Ala^{1834}$ (HMAPTKDEFDCKA) (SEQ ID NO:6), $Thr^{1892}$-$Ala^{1901}$ (TENMERNCRA) (SEQ ID NO:7), $Glu^{1908}$-$His^{1909}$ (EDPTFKENYRFH) (SEQ ID NO:8), $Thr^{1964}$-$Lys^{1972}$ (TVRKKEEYK) (SEQ ID NO:9), $Lys^{2049}$-$Gly^{2057}$ (KLARLHYSG) (SEQ ID NO:10), and $Asp^{2108}$-$Gly^{2117}$ (DGKKWQTYRG) (SEQ ID NO:11) were synthesized by Fmoc (N-(9-fluorenyl)methoxycarbonyl) chemistry by the manual "T-bag"-method (Houghton, R. A. (1985) PNAS U.S.A. 82, 5131-5135; WO96/41816; incorporated herein by reference), or employing a 430A Applied Biosystems instrument (Pharmacia LKB Biotechnology, Roosendaal, the Netherlands; Medprobe AS, Oslo, Norway).

Peptides were more than 95% pure as determined by high-pressure-liquid-chromatography (HPLC) analysis, and their identity was confirmed by mass spectrometry. Purified placenta-derived LRP was obtained as described (Moestrup, S. K., and Gliemann, J. (1991) J. Biol. Chem. 266, 14011-14017; incorporated herein by reference). Gluthatione S-transferase-fused receptor-associated protein (GST-RAP) was expressed in *Escherichia coli* strain DH5a and purified employing gluthatione-sepharose as described (Herz, J., Goldstein, J. L., Strickland, D. K., Ho, Y. K., and. Brown, M. S. (1991) J. Biol. Chem. 266, 21232-21238; incorporated herein by reference). Baby Hamster Kidney (BHK) cells expressing recombinant LRP ligand binding clusters II and IV have been described previously (Neels, J. G. et al., (1999) supra). Human serum albumin (HSA) was from the Division of Products of CLB (Amsterdam, The Netherlands). Protein was quantified by the method of Bradford (Bradford, M. M. (1976) Anal. Biolchem. 72, 248-254; incorporated herein by reference), using HSA as a standard.

Recombinant Proteins—

The plasmid pCLB-BPVdB695 encoding the FVIII B domain deletion variant, FVIII-del (868-1562) has been described previously (Mertens, K., Donath, M. J. S. H., van Leen, R. W., de Keyzer-Nellen, M. J. M., Verbeet, M. P., Klaasse Bos, J. M., Leyte, A., and van Mourik, J. A. (1993) Br. J. Haematol. 85, 133-142; incorporated herein by reference), and was used as a template to construct the plasmid coding for $FVIII/FV^{1811-1818}$ chimera. Oligonucleotide primers derived from the FVIII light chain sequence containing the FVIII/FV codon replacements (Table II below), were employed to construct the plasmids using the Overlap Extension PCR mutagenesis method (Tao, B. Y., and Lee K. C. P. (1994) PCR Technology Current Innovations (Griffin, H. G., and Griffin, A. M., eds), 71-72, CRC Press, Boca Raton, Fla.; incorporated herein by reference). Sequence analysis was performed to verify the presence of the mutations in the plasmid. Transfection of FVIII encoding plasmids into murine fibroblasts (C127) cells was performed as described previously (Mertens, K., et al., (1993), supra). Stable cell lines expressing wild-type FVIII or $FVIII/FV^{1811-1818}$ chimera were maintained in 1-I cell factories in RPMI 1640 medium, supplemented with 5% FCS, 100 U/ml penicillin, 100 µg/ml streptomycin, 1 µg/ml amphotericin B and 0.8 µg/ml desoxycholate. FVIII containing medium was harvested three times a week. Medium was subsequently filtered to remove cell debris and concentrated approximately 10-fold employing a hollow fiber cartridge (Hemoflow F5, Fresenius, Bad Homburg, Germany). Benzamidine was added to a final concentration of 10 mM, and concentrates were stored at −20° C. FVIII was purified from concentrated medium by immunoaffinity chromatography employing antibody CLB-CAg 117 and Q-Sepharose chromatography according to an established procedure (Mertens, K., et al., (1993), supra). FVIII light chains were prepared by incubating purified FVIII/$FV^{1811-1818}$ chimera and wild-type FVIII in a buffer containing 40 mM EDTA, 100 mM NaCl, and 50 mM Tris (pH 7.4) for 4 h at 25° C. Subsequently, $FVIII/FV^{1811-1818}$ light chain chimera and wild-type FVIII light chain were purified employing Q-Sepharose chromatography. Recombinant proteins were eluted in a buffer containing 1 M NaCl and 50 mM Tris (pH 7.4), dialyzed against 150 mM NaCl and 50 mM Tris (pH 7.4), and stored at 4° C. The construction of the plasmid encoding the recombinant C2 domain (i.e. residues $Ser^{2173}$-$Tyr^{2332}$) has been described previously (Fijnvandraat, K., et al., (1998) supra). The plasmid pACgp67b-His-a3-A3-C1, encoding the FVIII a3-A3-C1 fragment (i.e. residues $Glu^{1649}$-$Asn^{2172}$) was constructed by polymerase chain reaction employing the oligonucleotide primers, 5'-TTACTC-GAGGAAATMCTCGTACTACTC-3' (sense) (SEQ ID NO:13), and, 5'-AATGCGGCCGCTTCAATTTAAATCA-CAGCCCAT-3' (anti-sense) (SEQ ID NO:14), using pCLB-BPVdB695 as a template (Mertens, K., et al., (1993), supra). The amplified DNA fragment was purified, digested with XhoI and NotI, and ligated into pBluescript. The resulting construct was verified by sequencing. Subsequently, pBluescript-a3-A3-C1 was digested with EspI and NotI, and the obtained fragment was purified and ligated into the EspI/NotI digested pACgp67b-80K plasmid (Fijnvandraat, K., Turenhout, E. A. M., van den Brink, E. N., ten Cate, J. W., van Mourik, J. A., Peters, M., and Voorberg, J. (1997) Blood 89, 4371-4377; incorporated herein by reference). A DNA fragment encoding a poly His-tag (5'-ATTGGATCCGGCCAT-CATCATCATCATCATGGCGGCAGC-CCCCGCAGCTTTC AMAGCCCGGGGCCATGGGA-3') (SEQ ID NO:15) was digested with BamHI and NcoI and cloned within the BamHI/NcoI digested pACgp67b-a3-A3-C1 plasmid. Using the baculovirus expression system, recombinant a3-A3-C1 and C2 fragments were obtained by infection of insect cells as described (Fijnvandraat, K., et al., (1998), supra). The a3-A3-C1 fragment was purified from Insect-XPRESS medium employing immunoaffinity chromatography, using the anti-A3 domain antibody CLB-CAgA coupled to CNBr-Sepharose 4B as affinity matrix. CLB-CAg A-Sepharose was incubated with medium containing the a3-A3-C1 fragment for 16 h at 4° C. After binding, the immunoaffinity matrix was collected and washed with a buffer containing 1 M NaCl and 50 mM Tris (pH 7.4), and eluted with 150 mM NaCl, 55% (v/v) Ethylene Glycol, and 50 mM Lysine (pH 11). Elution fractions were immediately neutralized with 1 M Imidazole (pH 6.0), dialyzed against 150 mM NaCl, 50% (v/v) Glycerol, and 50 mM Tris (pH 7.4), and stored at −20° C. The recombinant C2 domain was purified employing the same immunoaffinity chromatography technique, except that anti-C2 domain antibody CLB-CAg 117 was used instead of CLB-CAg A.

Purification of Factor Va Light Chain—Human Factor V (FV) was obtained from human plasma provided by our institute (CLB, The Netherlands). Full-length FV was purified employing immunoaffinity chromatography. FVa light chain was prepared by incubating FV (10 µM) with thrombin (2 µM) in a buffer containing 100 mM NaCl, 5 mM $CaCl_2$, and 50 mM Tris (pH 7.4) for 2 h at 37° C. Thrombin was inactivated by Hirudin (Sigma-Aldrich, St. Louis, Mo.) and FVa light chain was purified employing immunoaffinity chromatography, using CNBr-Sepharose 4B coupled with the anti-Factor V light chain monoclonal antibody CLB-FV 5 (5 mg/ml). The immunoaffinity matrix was washed with 100 mM NaCl, 25 mM EDTA, and 50 mM Tris (pH 7.4) and eluted with 100 mM NaCl, 5 mM $CaCl_2$, 55% (v/v) Ethylene Glycol, and 50 mM Tris (pH 7.4). Purified FVa light chain was dialyzed against 150 mM NaCl, 5 mM $CaCl_2$, 50% (v/v) glycerol, and 50 mM Tris (pH 7.4), and stored at −20° C.

Expression and Purification of Recombinant LRP Fragments—

Recombinant LRP clusters II and IV were expressed in BHK cells, using Optimem I medium supplemented with 100 units/ml penicillin and 100 µg/ml streptomycin (Neels, J. G., et al., (1999) supra). After harvesting of the medium, $CaCl_2$ was added to a final concentration of 10 mM. Purification of LRP clusters II and IV from conditioned media was performed by a single purification step, using GST-RAP coupled to CNBr-Sepharose 4B as affinity matrix. The matrix was collected in a column, washed with a buffer containing 150 mM NaCl, 5 mM $CaCl_2$, and 50 mM Hepes (pH 7.4), and eluted with 150 mM NaCl, 20 mM EDTA, and 50 mM Hepes (pH 7.4). Subsequently, purified LRP cluster preparations were concentrated employing Centricon 10 concentrators (Millipore, Bedford, Mass.) by successive rounds of centrifugation for 1 h at 4000×g at 4° C. Finally, the preparations were dialyzed against 150 mM NaCl, 2 mM $CaCl_2$, 0.005% (v/v) Tween® 20, and 20 mM Hepes (pH 7.4), and stored at 4° C.

Solid-Phase Binding Assays—

Recombinant LRP clusters II or IV (1 pmol/well) were adsorbed onto microtiter wells in 50 mM $NaHCO_3$ (pH 9.8) in a volume of 50 µl for 16 h at 4° C. Wells were blocked with 2% (w/v) HSA, 150 mM NaCl, 5 mM $CaCl_2$, and 50 mM Tris (pH 7.4) in a volume of 200 µl for 1 h at 37° C. After three rapid washes (less than 5 seconds each) with 150 mM NaCl, 5 mM $CaCl_2$, 0.1% (v/v) Tween® 20, and 50 mM Tris (pH 7.4), FVIII light chain or its derivatives were incubated at various concentrations in a volume of 50 µl in a buffer containing 150 mM NaCl, 5 mM $CaCl_2$, 1% (w/v) HSA, 0.1% (v/v) Tween® 20, and 50 mM Tris (pH 7.4) for 2 h. at 37° C. Bound ligand was detected by incubating with peroxidase-conjugated monoclonal antibody CLB-CAg 12 in the same buffer for 15 min at 37° C. Antibody CLB-CAg 12 did not interfere with binding of FVIII fragments to LRP or LRP clusters (data not shown). In competition experiments, FVIII light chain (25 nM) was incubated with wells containing immobilized LRP clusters, either in the presence or absence of serial dilutions of competitor in a volume of 50 µl for 2 h at 37° C. Residual FVIII binding was detected as described above. Data were corrected for binding to empty microtiter wells, which was less than 5% relative to binding to wells containing immobilized LRP clusters.

Surface Plasmon Resonance—

The kinetics of protein interactions was determined by surface plasmon resonance (SPR) analysis, employing a BIAcore™2000 biosensor system (Biacore AS, Uppsala, Sweden). LRP (16 fmol/$mm^2$), FVIII light chain (71 fmol/$mm^2$), a3-A3-C1 fragment (67 fmol/$mm^2$), FVa light chain (76 fmol/$mm^2$), or scFv EL14 (67 fmol/$mm^2$) were covalently coupled to the dextran surface of an activated CM5-sensor chip via primary amino groups, using the amine-coupling kit as prescribed by the supplier. One control flow-channel was routinely activated and blocked in the absence of protein. Association of analyte was assessed in 150 mM NaCl, 2 mM $CaCl_2$, 0.005% (v/v) Tween® 20, and 20 mM Hepes (pH 7.4) for 2 min, at a flow rate of 20 µl/min at 25° C. Dissociation was allowed for 2 min in the same buffer flow. Sensor-chips were regenerated using several pulses of either 100 mM $H_3PO_4$ or 20 mM EDTA, 1 M NaCl, and 50 mM Hepes (pH 7.4) at a flow rate of 20 µl/min. The association ($k_{on}$) and dissociation ($k_{off}$) rate constants were determined by using the BIAevaluation software 3.1 (Biacore AB, Uppsala, Sweden). Data were corrected for bulk refractive index changes and fitted by nonlinear regression analysis according to a two-site binding model. Equilibrium dissociation constants ($k_d$) were calculated from the ratio $k_{off}/k_{on}$. The $k_d$ value for low-affinity interactions was estimated using steady-state affinity analysis by using BIAevaluation software. In competition experiments, FVIII light chain (50 nM) was incubated with immobilized LRP (16 fmol/$mm^2$) either in the presence or absence of serial dilutions of competitor for 2 min, at a flow rate of 20 µl/min at 25° C.

Binding of FVIII/$FV^{1811-1818}$ Light Chain Chimera to LRP Cluster II—

The recombinant FVIII/$FV^{1811-1818}$ light chain chimera or the recombinant wild-type FVIII light chain were coupled to immobilized scFv EL14 till a density of 20 fmol/$mm^2$, in a buffer containing 150 mM NaCl and 50 mM Tris (pH 7.4). LRP cluster II (25-125 nM) was passed over separate channels with immobilized FVIII/$FV^{1811-1818}$ light chain chimera or wild-type recombinant FVIII light chain, respectively, and one control (scFv EL14-coated) channel in 150 mM NaCl, 2 mM $CaCl_2$, 0.005% (v/v) Tween® 20, and 20 mM Hepes (pH 7.4) for 2 min, at a flow rate of 20 µl/min at 25° C.

Results:

Interaction Between LRP and FVIII Light Chain Fragments—

The isolated FVIII C2 domain (i.e. residues $Ser^{2173}$-$Tyr^{2332}$) associates with LRP less effectively than intact FVIII light chain (Lenting, P. J., et al., (1999) supra; WO00/28021 supra). In this study, the possibility was explored that additional sites in the FVIII light chain contribute to LRP binding. To this end, the interaction of four FVIII derivatives with immobilized LRP, employing SPR analysis was monitored. These derivatives include the FVIII light chain, the a3-A3-C1 moiety (i.e. residues $Glu^{1649}$-$Asn^{2172}$), the C-terminal C2 domain, and a FVIII light chain fragment that lacks the N-terminal acidic region employing cleavage at position $Arg^{1721}$ by Factor Xa (i.e. residues $Ala^{1722}$-$Tyr^{2332}$).

As shown in FIG. 1, all FVIII fragments displayed time-dependent association with immobilized LRP followed by dissociation, which appeared to be dose-dependent as highest response was observed at highest LRP density (data not shown). A two-site binding model was required to appropriately describe the acquired data of the FVIII light chain, Factor Xa-cleaved light chain, and the a3-A3-C1 fragment. The calculated association ($k_{on}$) and dissociation ($k_{off}$) rate constants that follow from this model were in the same order of magnitude for these fragments (Table I below). This leads to comparable $K_d$ values describing a high and a slightly lower affinity interaction with immobilized LRP, namely 18 nM and 59 nM for the FVIII light chain, 22 nM and 60 nM for the Factor Xa-cleaved light chain, and 26 nM and 74 nM for the a3-A3-C1 derivative (Table I below). In contrast, the isolated C2 domain displayed a too fast dissociation rate to be accurately described by any of the binding models. The affinity ($K_d$) of this fragment (3.4 µM) was therefore estimated by extrapolation, employing steady-state affinity calculations. Collectively, these results show that there is a high affinity LRP binding site in the A3-C1 region (i.e. residues $Ala^{1722}$-$Asn^{2172}$) and a low affinity site in the C2 domain.

TABLE I

|  |  | $k_{off}$ $s^{-1}$ | $k_{on}$ $M^{-1}s^{-1}$ | $K_d$ nM |
|---|---|---|---|---|
| FVIII light chain | (1) | 2.8 (±0.7) × $10^{-3}$ | 1.6 (±0.3) × $10^5$ | 18 ± 6 |
|  | (2) | 6.9 (±1.4) × $10^{-2}$ | 1.2 (±0.2) × $10^6$ | 59 ± 15 |
| Factor Xa-cleaved light chain | (1) | 3.0 (±0.3) × $10^{-3}$ | 1.3 (±0.2) × $10^5$ | 22 ± 4 |
|  | (2) | 5.6 (±0.7) × $10^{-2}$ | 0.9 (±0.3) × $10^6$ | 60 ± 23 |
| a3-A3-C1 fragment | (1) | 4.1 (±0.7) × $10^{-3}$ | 1.6 (±0.4) × $10^5$ | 26 ± 7 |
|  | (2) | 8.0 (±0.7) × $10^{-2}$ | 1.1 (±0.3) × $10^6$ | 74 ± 20 |
| C2 domain | (1) | — | — | 3400 ± 200 |

(Note to Table I: Kinetic parameters for binding of FVIII light chain and its derivatives to immobilized LRP. Association and dissociation of various concentrations of FVIII light chain (10-250 nM), 67-kDa fragment (10-250 nM), a3-A3-C1 fragment (10-250 nM), or C2 domain (500-2000 nM) to immobilized LRP (16 fmol/mm2) were assessed as described in 'Experimental Procedures'. Obtained data were analyzed to calculate association rate constants ($k_{on}$) and dissociation rate constants ($k_{off}$) using a two-site binding model. Each class of binding sites is referred to as 1 and 2, respectively. Affinity constants ($K_d$) were calculated from the ratio $k_{off}/k_{on}$. The interaction between C2 domain and LRP was assessed employing steady-state affinity analysis. Data are based on three to six measurements using at least five different concentrations for each measurement. Data represent the average±S.D.)

Binding of FVIII Light Chain to Immobilized LRP Clusters II and IV—

A previous study showed that the LRP ligand binding clusters II and IV mediate the interaction with FVIII light chain (Neels, J. G., et al., (1999), supra). In the present study, a solid-phase binding assay to address the question whether or not LRP clusters II and IV can compete for binding to FVIII light chain was used. As demonstrated in the inset of FIG. 2, FVIII light chain was able to bind immobilized LRP cluster II in a dose-dependent manner. This observation is in agreement with the previous findings, in which SPR analysis was used to monitor the interaction between LRP cluster II and immobilized FVIII light chain (Neels, J. G., et al., (1999), supra). Competition studies revealed that LRP clusters II and IV compete for binding to the FVIII light chain (FIG. 2). LRP cluster II displayed a dose-dependent inhibition of FVIII light chain binding to immobilized LRP cluster IV. These data imply that LRP cluster II and IV share a similar binding region within the FVIII light chain.

Binding of LRP Cluster II to Immobilized FVa Light Chain—

Figure 3:
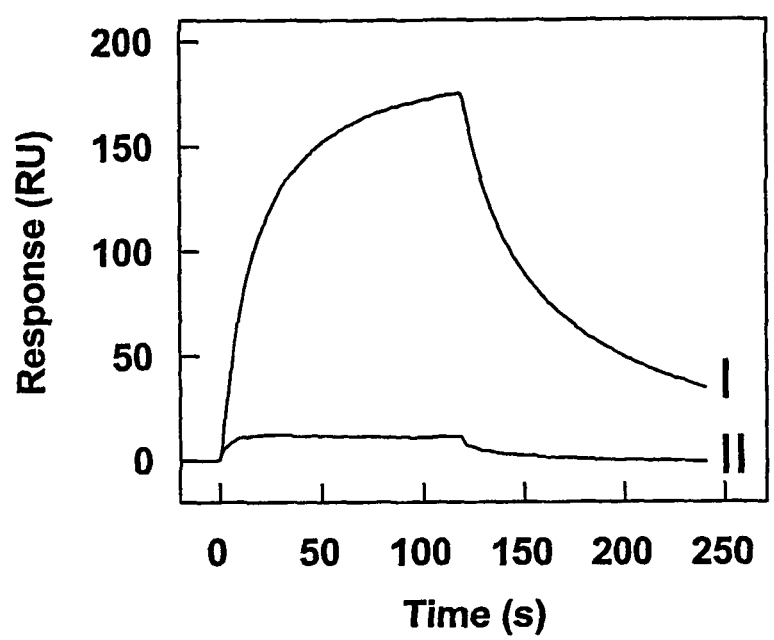

In view of the known homology between FVIII and FV (Church, W. R., et al., (1984), supra), the question may arise whether or not the light chains of FVIII and activated FV share binding properties to LRP cluster II. To this end, serial dilutions of LRP cluster II were incubated with immobilized FVII (light chain and FVa light chain. As shown in FIG. 3, the light chains of FVa and FVIII proved different in that only FVIII displayed high-affinity binding to LRP cluster II. These observations indicate that the a3-A3-C1 domains of the FVIII light chain contain a high affinity LRP interactive region that is not conserved in the FVa light chain.

Effect of Synthetic Peptides on FVIII Light Chain Binding to LRP Cluster II—

A panel of synthetic peptides was constructed that mimic the surface loops of the a3-A3-C1 domains (WO 96/41816, supra). The observation that the FVa light chain does not efficiently associate with LRP cluster II was used as a selection criterion for construction of synthetic peptides that are unique for FVIII. The solvent accessibility of these loops was verified employing hydropathy analysis (Lenting, P. J., et al., (1996), supra) and by studying the three-dimensional model of the intact FVIII heterodimer (Stoilova-McPhie, S., Villoutreix, B. O., Mertens, K., Kemball-Cook, G., and Holzenburg, A. (2002) Blood 99, 1215-1223; incorporated herein by reference). The synthetic peptides comprised residues $Trp^{1707}$-$Arg^{1721}$ (SEQ ID NO:5), $Lys^{1804}$-$Lys^{1818}$ (SEQ ID NO:2), $Tyr^{1815}$-$Ala^{1834}$ (SEQ ID NO:3), $His^{1822}$-$Ala^{1834}$ (SEQ ID NO:6), $Thr^{1892}$-$Ala^{1901}$ (SEQ ID NO:7), $Glu^{1908}$-$His^{1919}$ (SEQ ID NO:8), $Thr^{1964}$-$Lys^{1972}$ (SEQ ID NO:9), $Lys^{2049}$-$Gly^{2057}$ (SEQ ID NO:10), and $Asp^{2108}$-$Gly^{2117}$ (SEQ ID NO:11) (Table II).

TABLE II

| Domain | Residues | $IC_{50}$ | Sequence |
|---|---|---|---|
| A3 | 1707-1721 | >1 mM | WDYGMSSSPHVLRNR |
| A3 | 1804-1818 | 1.9 ± 0.2 µM | KNFVKPNETKTYFWK |
| A3 | 1815-1834 | 16.8 ± 0.4 µM | YFWKVQHHMAPTKDEFDCKA |
| A3 | 1822-1834 | >1 mM | HMAPTKDEFDCKA |
| A3 | 1892-1901 | >1 mM | TENMERNCRA |
| A3 | 1908-1919 | >1 mM | EDPTFKENYRFH |
| A3 | 1964-1972 | >1 mM | TVRKKEEYK |
| C1 | 2049-2057 | >1 mM | KLARLHYSG |
| C1 | 2108-2117 | 0.9 ± 0.3 mM | DGKKWQTYRG |

(Note to Table II: Effect of FVIII a3-A3-C1 fragment derived synthetic peptides on the interaction between FVIII light chain and LRP cluster II. FVIII light chain (25 nM) was incubated with immobilized LRP cluster II (1 pmol/well) in a volume of 50 µl in 150 mM NaCl, 5 mM CaCl2, 1% (w/v) HSA, 0.1% Tween® 20, and 50 mM Tris (pH 7.4) in the presence or absence of various concentrations of synthetic peptide (0-1 mM) for 2 h at 37° C. After washing with the same buffer, bound FVIII light chain was quantified by incubation with peroxidase-conjugated anti-FVIII antibody CLB-CAg 12 for 15 min at 37° C. Half-maximum inhibition constants ($IC_{50}$) represent the mean values±S.D. of three experiments.)

Subsequently, these peptides were tested for their ability to interfere with the interaction between FVIII light chain and immobilized LRP cluster II. As shown in Table II, the synthetic peptides $Lys^{1804}$-$Lys^{1818}$ (SEQ ID No: 2) and $Tyr^{1815}$-

Ala$^{1834}$ (SEQ ID No:3) efficiently inhibited the interaction of FVIII light chain and immobilized LRP cluster II. Half-maximum inhibition ($CO_{50}$) was reached at peptide concentrations of about 1.9 and 16.8 µM, respectively. The other synthetic peptides did not show such an inhibitory effect. These observations suggest that the sequence Lys$^{1804}$-Ala$^{1834}$ within the A3 domain of FVIII contains important residues involved in the interaction with LRP.

Effect of scFv Antibody Fragments on FVIII Light Chain Binding to LRP and its Cluster II—

Previously, a phage-display to isolate recombinant scFv antibody fragments from a patient with inhibitory antibodies directed against residues within region Gln$^{1778}$-Asp$^{1840}$ (van den Brink, E. N., Turenhout, E. A. M., Bovenschen, N., Heijnen, B. G., Mertens, K., Peters, M., and Voorberg, J (2001), Blood 97, 966-972; Voorberg, J., et al., Method for diagnosis and treatment of haemophilia A patients with an inhibitor. International Patent Application WO 99/58680; incorporated herein by reference) was employed. These scFvs were evaluated for their ability to interfere with the interaction between FVIII light chain and LRP or cluster II. The first scFv, referred to as scFv KM36, is directed against a region within Gln$^{1778}$-Asp$^{1840}$, but does not require residues Arg$^{1803}$-Lys$^{1818}$ for FVIII binding (van den Brink, et al., (2001), supra; WO 99/58680, supra). The second scFv, designated as scFv KM41, is directed against region Arg$^{1803}$-Lys$^{1818}$ and inhibits FVIII procoagulant activity (van den Brink et al., (2001), supra; WO 99/58680 supra). The amino acid sequence of the heavy chain of scFv KM41 SEQ ID NO:17) as well as the corresponding DNA sequence is shown in SEQ ID NO:16. The amino acid sequence of the light chain of scFv KM41 (SEQ ID NO:19) as well as the corresponding DNA sequence is shown in SEQ ID NO:18. The heavy chain and light chain of KM41 can be bound over a peptide linker (SEQ ID NO:24) and can have a histidine tag at the C-terminus. The amino acid sequence of the expressed scFv KM41 protein is depicted in SEQ ID NO:25. The third scFv, called scFv KM33 is similar to scFv KM41 except that it does not require A3 domain region 1778-1818 for its interaction with FVIII light chain (van den Brink et al., (2001), supra; WO 99/58680 supra). The amino acid sequence of the heavy chain of scFv KM33 (SEQ ID NO:21) as well as the corresponding DNA sequence is shown in SEQ ID NO:20. The amino acid sequence of the light chain of scFv KM33 (SEQ ID NO:23) as well as the corresponding DNA sequence is shown in SEQ ID NO:22. The heavy chain and light chain of KM33 can be bound over a peptide linker (SEQ ID NO:24) and can have a histidine tag at the C-terminus. The amino acid sequence of the expressed scFv KM33 protein is depicted in SEQ ID NO:26. As shown in FIG. 4A, scFv KM36 did not affect the interaction between FVIII light chain and immobilized LRP cluster II. In contrast, the presence of scFv KM41 inhibited the binding of FVIII light chain to LRP cluster II (FIG. 4A). The effect of scFv KM41 on the interaction between FVIII light chain and LRP was further studied employing SPR analysis. As shown in FIG. 4B, association of FVIII light chain with immobilized LRP was inhibited in the presence of scFv KM41. As demonstrated in FIG. 5, scFv KM33 effectively inhibited FVIII light chain binding to immobilized LRP cluster II, in a dose-dependent manner. The apparent inhibition constant was about 5 nM, which is similar to the $K_d$ value for the binding of the FVIII light chain to the same scFv (van den Brink et al., (2001), supra; WO 99/58680 supra). These data strongly suggest that scFv KM33, scFv KM41, and LRP share overlapping binding sites within the light chain of FVIII.

The FVIII Light Chain Sequence Glu$^{1811}$-Lys$^{1818}$ Contains a Binding Site for LRP—

The synthetic peptides Lys$^{1804}$-Lys$^{1818}$ and Tyr$^{1815}$-Ala$^{1834}$ are effective inhibitors of FVIII procoagulant activity by interfering with the assembly of the FVIIIa-FIXa complex (Lenting, P. J., et al., (1996) supra; WO 96/41816, supra), while the scFvs KM33 and KM41 are effective inhibitors of FVIII procoagulant activity by interfering with the assembly of the FVIIIa-FIXa complex (Lenting, P. J., et al., (1996) supra; van den Brink et al., (2001), supra; WO 99/58680, supra). As FVIII A3 domain residues Glu$^{1811}$-Lys$^{1818}$ contributes to the interaction with FIXa (Lenting, P. J., et al., (1996) supra; WO 96/41816, supra), this particular FVIII light chain region was investigated with respect to its role in the interaction with LRP. As FVa light chain did not interact with LRP cluster II, a FVIII light chain chimera was constructed in which residues Glu$^{1811}$-Lys$^{1818}$ were replaced by corresponding residues of FV (i.e. residues $^{1704}$SSY-TYVWH$^{1711}$; (SEQ ID NO:12)). The isolated chimera (FVIII/FV$^{1811}$-1818) was compared to wild-type recombinant FVIII light chain in terms of association with LRP cluster II, employing SPR analysis. As shown in FIG. 6, LRP cluster II displayed a 2-3 fold reduced association with immobilized FVIII/FV$^{1811}$-1818 as compared to wild-type FVIII light chain.

The isolated chimera (FVIII/FV$^{1811-1818}$) was then evaluated for its ability to interact with scFv KM41, employing SPR analysis. As demonstrated in FIG. 7, scFv KM41 did not recognize the immobilized FVIII/FV$^{1811-1818}$ chimera, whereas it readily reacted with immobilized wild-type recombinant FVIII light chain. These observations indicate that FVIII A3 domain region Glu$^{1811}$-Lys$^{1818}$ contains residues critical for binding to scFv KM41. These data demonstrate that FVIII light chain region Glu$^{1811}$-Lys$^{1818}$ serves an important role in the assembly of the LRP-FVIII light chain complex.

In the present study, it is demonstrated that A3 domain region Glu$^{1811}$-Lys$^{1818}$ of the FVIII light chain contributes to the high affinity interaction with LRP. Several lines of evidence support this conclusion. First, the A3 domain derived synthetic peptides Lys$^{1804}$-Lys$^{1818}$ and Tyr$^{1815}$-Ala$^{1834}$ affected the interaction between FVIII light chain and LRP cluster II (Table II). Second, a FVIII light chain chimera, in which region Glu$^{1811}$-Lys$^{1818}$ is replaced by corresponding residues of FV, displayed a reduction in association to LRP cluster II as compared to the wild-type FVIII light chain (FIG. 6). Third, a recombinant scFv antibody fragment, directed against region Glu$^{1811}$-Lys$^{1818}$, inhibited binding of FVIII light chain to LRP or its cluster II fragment (FIG. 4).

For a number of LRP ligands, including RAP, lipoprotein lipase, and $\alpha_2$-macroglobulin, it has been established that positively charged residues at the ligand surface are involved in the interaction with LRP (Melman, L., Cao, Z. F., Rennke, S., Paz Marzolo, M., Wardell, M. R., and Bu, G. (2001) J. Biol. Chem. 276, 29338-29346; Chappell, D. A., Fry, G. L., Waknitz, M. A., Muhonen, L. E., Platlet, M. W., Iverius, P. H., and Strickland, D. K. (1993) J. Biol. Chem. 268, 14168-14175; Howard, G. C., Yamaguchi, Y., Misra, U. K., Gawdi, G., Nelsen, A., DeCamp, D. L., and Pizzo, S. V. (1996) J. Biol. Chem. 271, 14105-14111; Nielsen, K. L., Holtet, T. L., Etzerodt, M., Moestrup, S. K., Gliemann, J., Sottrup-Jensen, L., and Thorgersen, H. C. (1996) J. Biol. Chem. 271, 12909-12912; incorporated herein by reference). Interestingly, also FVIII A3 domain region Glu$^{1811}$-Lys$^{1818}$ (i.e. residues $^{1811}$ETKTYFWK$^{1818}$ (SEQ ID NO:1)) contains two exposed positively charged lysine residues at positions 1813 and 1818. As compared to the homologue part within the A3 domain of FV (i.e. residues $^{1704}$SSYTYVWH$^{1711}$ (SEQ ID NO:12)), these lysine residues appear to be unique for the FVIII A3 domain (Church, W.R., et al. (1984), supra). Replacement of FVIII residues Glu$^{1811}$-Lys$^{1818}$ for the corresponding residues of FV resulted in impaired binding to LRP cluster II (FIG. 6). These results suggest that positively charged residues within region Glu$^{1811}$-Lys$^{1818}$ mediate an electrostatic interaction with LRP.

To date, two amino acid regions within the FVIII light chain have been identified that contribute to the assembly of the LRP-FVIII light chain complex. Besides a role for the A3 domain region Glu$^{1811}$-Lys$^{1818}$ found in this study, also the carboxyterminal C2 domain is known to contribute to the interaction with LRP (Lenting, P. J., Neels, J. G., van den Berg, B. M. M., Clijsters, P. P. F. M., Meijerman, D. W. E., Pannekoek, H., van Mourik, J. A., Mertens, K., and van Zonneveld, A.,-J. (1999) J. Biol. Chem. 274, 23734-23739; Lenting, P. J., et al. A factor VIII polypeptide with factor VIIILC-activity. International Patent Application WO 00/28021; incorporated herein by reference). The LRP interactive site in the A3 domain seems more predominant than the one in the C2 domain, as the isolated C2 domain exhibited a low affinity interaction with LRP ($K_d \approx 3.4$ µM) (Table I). This is in agreement with a previous study in which the isolated C2 domain showed only modest association with LRP (Lenting, P. J. et al., (1999), supra; WO 00/28021, supra). In addition, the affinity for FVIII light chain binding to LRP is not affected upon deletion of the C2 domain (Table I). However, it was demonstrated that an anti-C2 domain monoclonal antibody (ESH4) completely inhibits the interaction between FVIII light chain and LRP (Lenting, P. J. et al., (1999), supra; WO 00/28021, supra). The mechanism by which antibody ESH4 inhibits LRP binding is not yet elucidated. Because the anti-C2 antibody does not require region Glu$^{1811}$-Lys$^{1818}$ for its interaction with FVIII light chain (Scandella, D., Gilbert, G. E., Shima, M., Nakai, H., Eagleson, C., Felch, M., Prescott, R., Rajalakshmi, K. J., Hoyer, L. W., and Saenko, E. (1995) Blood 86, 1811-1819; incorporated herein by reference), it is unlikely that ESH4 competes with LRP for binding to the same site in the A3 domain. Therefore, one of the mechanisms that could contribute to the inhibition includes sterical interference.

In contrast, scFv KM41 only partially inhibits the interaction between FVIII light chain and LRP (FIG. 4). This might be due to the relative small size of a scFv antibody fragment ($\approx$30 kDa) as compared to a complete antibody ($\approx$150 kDa). These observations suggest that besides region Glu$^{1811}$-Lys$^{1818}$ other surface exposed structural elements within the A3-C1 domains (i.e. residues Ala$^{1722}$-Asn$^{2172}$) contribute to the assembly of the LRP-FVIII light chain complex. This is in line with the observation that the FVIII/FV$^{1811-1818}$ light chain chimera demonstrated residual binding to LRP cluster II (FIG. 6). In this context it should be mentioned that the Glu$^{1811}$-Lys$^{1818}$ region within the A3 domain of FVIII light chain is part of a larger segment that is exposed to the protein surface (i.e. residues Glu$^{1804}$-Lys$^{1818}$) (Lenting, P. J., et al., (1996), supra). Besides the lysine residues at positions Lys$^{1813}$ and Lys$^{1818}$, this region contains two additional FVIII unique lysine residues at positions Lys$^{1804}$ and Lys$^{1808}$, which might play a role in the interaction with LRP.

EXAMPLE II

Experimental procedure: vWF knock out mice (decreased endogenous Factor VIII, 20% Factor VIII compared to healthy animals) were treated with human recombinant Factor VIII (Recombinate™; 200 U/kg) and recombinant scFv (KM33) in excess. (30 nM versus 3 nM Factor VIII in plasma). In control experiments, Factor VIII and a control scFv fragment (KM38) binding to a different domain as the proposed LRP binding site on the Factor VIII molecule were used in the same concentrations. Infusion of recombinant FVIII without any addition was used to monitor the clearance of Factor VIII in this model system.

At defined time points (15, 30, 60, 120 and 240 minutes) after injection, blood was collected by heart puncture, plasma was subsequently isolated, shock frozen and analyzed for Factor VIII activity. Ten mice were used at each time point, plasma was diluted to 3 concentrations (1:20, 1:60 and 1:100) and analyzed in duplicate. Factor VIII levels were quantified by performing a quantitative ELISA.

Results: Data from the Factor VIII control group showed Factor VIII activities of 0.35 U/mL at 15 minutes, which corresponds to a recovery of 14%. At 30 minutes Factor VIII activity decreased to approximately 0.2 U/mL, which is the Factor VIII activity background of these mice (corresponding recovery of 8%). No further alteration of the FVIII concentration was detected at the following time points. The data indicate that in this mouse system, recombinant Factor VIII is cleared from the animal circulation within the first 30 minutes.

Analysis of plasma samples derived from mice treated with FVIII and the LRP blocking scFv-fragment (KM33) demonstrated that 15 minutes after application about 0.8 U/mL of Factor VIII could be detected. This translated into a recovery of 30.4%. Levels of Factor VIII activity decreased during the next 15 minutes to 0.5 U/mL (20% recovery) and reached 0.35 U/mL (14% recovery) after 60 minutes. Four hours after injection, FVIII activity levels reached the background activity of mouse Factor VIII. This high amount of FVIII activity within the circulation after 15 and 30 minutes, compared to the FVIII control group, indicates an extremely good protection from clearance of FVIII.

A second control group of animals received human FVIII co-injected with a scFv fragment (KM38) binding to Factor VIII on a site different than LRP. With these animals, the same results as with the Factor VIII control group were obtained (FIG. 8).

Employing an antibody fragment interfering with the FVIII-LRP interaction, it was possible to significantly increase the half-life of Recombinate™ in vWF knock-out mice. Furthermore, it could clearly be demonstrated that the recovery of human FVIII in the murine vWF-KO system could be more than doubled.

Variations within the purview of one skilled in the art are to be considered to fall within the scope of the present invention. Unless defined otherwise, all technical and scientific terms used herein have the same meaning as commonly understood by one of ordinary skill in the art to which this invention belongs. Although any methods and materials similar or equivalent to those describes herein can be used in the practice or testing of the present invention, the preferred methods and materials are now described.

What we claim:

1. A method of treating a patient suffering from a bleeding disorder, wherein the method comprises administering to the patient a pharmaceutical composition that comprises an antibody against the A3-C1 region of Factor VIII and at least one selected from the group consisting of a physiologically acceptable excipient, carrier, diluent, and stabilizator.

2. The method according to claim 1, wherein the bleeding disorder is Haemophilia A, von Willebrand's disease, or a temporary impairment of blood coagulation during or after a surgical procedure.

3. The method according to claim 1, wherein the antibody comprises a light chain comprising the amino acid sequence according to SEQ ID NO: 23 and a heavy chain comprising the amino acid sequence according to SEQ ID NO: 21.

4. The method according to claim 1, wherein the antibody is KM33 antibody (SEQ ID NO: 26).

5. The method according to claim 1, wherein the pharmaceutical composition comprises an antibody against the C1 domain of the Factor VIII.

* * * * *

UNITED STATES PATENT AND TRADEMARK OFFICE
CERTIFICATE OF CORRECTION

| | | Page 1 of 1 |
|---|---|---|
| PATENT NO. | : 8,586,538 B2 | |
| APPLICATION NO. | : 10/512907 | |
| DATED | : November 19, 2013 | |
| INVENTOR(S) | : Koenraad Mertens et al. | |

It is certified that error appears in the above-identified patent and that said Letters Patent is hereby corrected as shown below:

On the Title Page, Item (75) correct the following information under "Inventors":

delete "Jan Voorberg" and insert --Johannes Jacobus Voorberg--;

delete "Gaenserndorf" and insert --Korneuburg--.

Signed and Sealed this
Twenty-fifth Day of February, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,586,538 B2  Page 1 of 1
APPLICATION NO. : 10/512907
DATED : November 19, 2013
INVENTOR(S) : Mertens et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2620 days.

Signed and Sealed this
Twenty-second Day of September, 2015

Michelle K. Lee
*Director of the United States Patent and Trademark Office*